US012285154B2

(12) United States Patent
Comee et al.

(10) Patent No.: US 12,285,154 B2
(45) Date of Patent: Apr. 29, 2025

(54) INTERFACE AND MOTION TRANSLATION DEVICES, SYSTEMS, AND METHODS FOR ENDOSCOPE VALVES

(71) Applicant: Boston Scientific Scimed, Inc., Maple Grove, MN (US)

(72) Inventors: Shaun D. Comee, Fiskdale, MA (US); Ryan V. Wales, Northborough, MA (US); Laura E. Christakis, Framingham, MA (US); Rossana Zotti, Miami, FL (US); Kyle P. Moore, Hopkinton, MA (US); Laura E. Richards, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 158 days.

(21) Appl. No.: 17/208,706

(22) Filed: Mar. 22, 2021

(65) Prior Publication Data

US 2021/0298567 A1    Sep. 30, 2021

Related U.S. Application Data

(60) Provisional application No. 62/994,024, filed on Mar. 24, 2020, provisional application No. 62/994,018, (Continued)

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/015* (2013.01); *A61B 1/12* (2013.01);
(Continued)

(58) Field of Classification Search
CPC ............ A61B 1/00068; A61B 1/00082; A61B 1/00091; A61B 1/00094; A61B 1/00119;
(Continued)

(56) References Cited

U.S. PATENT DOCUMENTS 4,061,250 A * 12/1977 Tada .................... B05B 11/1014
                                                      251/321
4,694,821 A *  9/1987 Kondo ............... A61B 1/00068
                                                      600/158
(Continued)

FOREIGN PATENT DOCUMENTS

EP      2431062 A1     3/2012
JP   2000217777 A      8/2000
(Continued)

OTHER PUBLICATIONS

International Search Report and Written Opinion for the International Patent Application No. PCT/US2021/023479, mailed Jul. 9, 2021, 12 pages.
(Continued)

*Primary Examiner* — Ryan N Henderson
(74) *Attorney, Agent, or Firm* — Seager, Tufte & Wickhem, LLP

(57) ABSTRACT

Various embodiments are generally directed to devices, systems, and methods for controlling the flow of fluids in endoscopic systems, such as endoscopic ultrasound (EUS) endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve
(Continued)

control motions. In one or more embodiments, the valve sets and/or valve interface mechanisms may be disposable.

5 Claims, 38 Drawing Sheets

Related U.S. Application Data filed on Mar. 24, 2020, provisional application No. 62/994,008, filed on Mar. 24, 2020, provisional application No. 62/994,019, filed on Mar. 24, 2020, provisional application No. 62/994,021, filed on Mar. 24, 2020, provisional application No. 62/994,015, filed on Mar. 24, 2020.

(51) Int. Cl.
*A61B 1/12* (2006.01)
*F16K 21/20* (2006.01)
*A61B 1/018* (2006.01)

(52) U.S. Cl.
CPC .......... *F16K 21/20* (2013.01); *A61B 1/00082* (2013.01); *A61B 1/018* (2013.01)

(58) Field of Classification Search
CPC . A61B 1/00128; A61B 1/00137; A61B 1/015; A61B 1/018; A61B 1/12; A61B 1/126; A61B 1/127; F16K 21/20
See application file for complete search history.

(56) References Cited

U.S. PATENT DOCUMENTS

| | | | | |
|---|---|---|---|---|
| 4,736,732 | A * | 4/1988 | Shimonaka | A61M 1/7413 |
| | | | | 600/158 |
| 4,794,913 | A * | 1/1989 | Shimonaka | A61M 1/7413 |
| | | | | 600/154 |
| 4,800,869 | A * | 1/1989 | Nakajima | A61B 1/00068 |
| | | | | 600/158 |
| 6,334,844 | B1 * | 1/2002 | Akiba | A61B 1/00068 |
| | | | | 600/156 |
| 6,346,075 | B1 | 2/2002 | Arai et al. | |
| 8,273,014 | B2 * | 9/2012 | Ushijima | G02B 23/2476 |
| | | | | 600/152 |
| 8,568,303 | B2 * | 10/2013 | Yamane | A61B 1/12 |
| | | | | 600/156 |
| 2010/0049001 | A1 * | 2/2010 | Yamane | A61B 1/015 |
| | | | | 600/159 |
| 2011/0208003 | A1 * | 8/2011 | Yamane | A61B 1/12 |
| | | | | 600/159 |
| 2011/0298169 | A1 * | 12/2011 | Nguyen | A61B 1/125 |
| | | | | 269/86 |
| 2012/0088973 | A1 * | 4/2012 | Morimoto | A61B 1/00068 |
| | | | | 600/156 |
| 2012/0088975 | A1 * | 4/2012 | Morimoto | A61B 1/00068 |
| | | | | 600/159 |
| 2015/0305599 | A1 * | 10/2015 | Murayama | A61B 1/00119 |
| | | | | 600/159 |
| 2016/0302646 | A1 * | 10/2016 | Hamazaki | A61B 1/00 |
| 2018/0361034 | A1 * | 12/2018 | Tobien | F16K 31/5245 |
| 2019/0125167 | A1 * | 5/2019 | Taniguchi | A61B 1/015 |
| 2019/0350441 | A1 * | 11/2019 | Saiga | A61B 1/00068 |
| 2019/0350444 | A1 * | 11/2019 | Saiga | A61B 1/00068 |
| 2019/0350445 | A1 * | 11/2019 | Saiga | G02B 23/2476 |
| 2019/0350446 | A1 * | 11/2019 | Saiga | A61B 1/00068 |
| 2020/0016637 | A1 * | 1/2020 | Still | A61B 1/125 |
| 2020/0187756 | A1 * | 6/2020 | Maurice | A61B 1/126 |
| 2020/0355281 | A1 * | 11/2020 | Harris | A61M 39/16 |
| 2020/0375434 | A1 * | 12/2020 | Scutti | A61B 1/00137 |
| 2020/0386330 | A1 * | 12/2020 | Stanton | F16K 11/0712 |
| 2021/0007586 | A1 * | 1/2021 | Gavalis | A61B 1/125 |
| 2021/0076910 | A1 * | 3/2021 | Saiga | A61B 8/12 |
| 2021/0076914 | A1 * | 3/2021 | Arai | G02B 23/24 |

FOREIGN PATENT DOCUMENTS

| | | |
|---|---|---|
| JP | 2007111266 A | 5/2007 |
| WO | 2019225562 A1 | 11/2019 |

OTHER PUBLICATIONS

International Search Report and Written Opinion for the International Patent Application No. PCT/US2021/023482, mailed Jul. 9, 2021, 12 pages.
International Search Report and Written Opinion for the International Patent Application No. PCT/US2021/023484, mailed Jul. 9, 2021, 12 pages.
International Search Report and Written Opinion for the International Patent Application No. PCT/US2021/023478, mailed Jun. 10, 2021, 49 pages.

* cited by examiner

100

SUCTION VALVE ASSEMBLY 102

SUCTION VALVE WELL 104

SUCTION CHANNEL 106

WORKING CHANNEL 108

BALLOON CHANNEL 114

ATMOSPHERIC CHANNEL 116

SUCTION VALVE SET 118

WORKING CHANNEL VALVE 120

BALLOON VALVE 122

ATMOSPHERIC VALVE 124

VALVE INTERFACE MECHANISM 126

BIASING MEMBER SET 128

USER INTERFACE MECHANISM 130

AIR/WATER (AW) VALVE ASSEMBLY 202

AW VALVE SET 204

| AIR INPUT CHANNEL 206 | WATER INPUT CHANNEL 208 | AIR OUTPUT CHANNEL 210 |
| WATER OUTPUT CHANNEL 212 | BALLOON CHANNEL 214 | ATMOSPHERIC CHANNEL 216 |

AW VALVE SET 218

| PRIMARY CONTROL VALVE 220 | AIR INPUT VALVE 222 | ATMOSPHERIC VALVE 224 |

VALVE INTERFACE MECHANISM 226

| BIASING MEMBER SET 228 | USER INTERFACE MECHANISM 230 |

AIR INPUT VALVE OPEN STATE 1115-1

1200A

PRIMARY VALVE SEALED STATE 1215-1

INTERFACE AND MOTION TRANSLATION DEVICES, SYSTEMS, AND METHODS FOR ENDOSCOPE VALVES

PRIORITY

The present application claims the benefit of priority under 35 U.S.C. § 119 to U.S. Provisional Application Ser. Nos. 62/994,008, 62/994,015, 62/994,018, 62/994,019, 62/994,021, and 62/994,024, each filed Mar. 24, 2020, the disclosures of which are incorporated herein by reference in their entirety.

FIELD

The present disclosure relates generally to the field of medical devices. In particular, the present disclosure relates to devices, systems, and methods to control flow through a valve well for an endoscope.

BACKGROUND

An endoscopy procedure is used in medicine to access the interior of a body for diagnostic and/or therapeutic procedures. Oftentimes, the endoscopy procedure uses an endoscope to examine or manipulate the interior of a hollow organ or cavity of the body. Unlike many other medical imaging techniques, endoscopes are inserted directly into the organ. Typically, an endoscope includes one or more channels for the flow of one or more fluids therethrough. For example, one or more of suction, air, and water may flow through an endoscope. A valve assembly may be configured and used in various fashion to control the flow of the one or more fluids through the endoscope. In the case of an echoendoscope or ultrasound endoscope, control of fluids may also be used to inflate and deflate a balloon at the end of an endoscope.

It is with these considerations in mind that a variety of advantageous outcomes may be realized by the devices, systems and methods of the present disclosure.

SUMMARY

In one aspect, the present disclosure relates to a medical device comprising a suction valve set and a valve interface mechanism. The suction valve set may include a working channel valve, a balloon valve, and an atmospheric valve. The working channel valve may be configured to control flow through a working channel of a valve well, the balloon valve may be configured to control flow through a balloon channel of the valve well, and the atmospheric valve may be configured to control flow through an atmospheric channel of the valve well. The valve interface mechanism may include a set of one or more biasing members and a user interface mechanism. The user interface mechanism may be operable between a first state, a second state, and a third state, the first state comprising the suction valve set configured to place the suction channel in fluid communication with the atmospheric channel, the second state comprising the suction valve set configured to place the suction channel in fluid communication with the working channel, and the third state comprising the suction valve set configured to place the suction channel in fluid communication with the balloon channel. In the first state, the working channel valve may block flow through the working channel, the balloon valve may block flow through the balloon channel, and the atmospheric valve may permit flow through the atmospheric channel. In the second state, the working channel valve may permit flow through the working channel, the balloon valve may block flow through the balloon channel, and the atmospheric valve may block flow through the atmospheric channel. In the third state, the working channel valve may block flow through the working channel, the balloon valve may permit flow through the balloon channel, and the atmospheric valve may block flow through the atmospheric channel. In various embodiments, the user interface mechanism may include a lever to receive input to operate the user interface mechanism between the first state, the second state, and the third state. In various such embodiments, the set of one or more biasing members may comprise a tension or a compression spring to bias the lever into the first state. In some embodiments, the user interface mechanism may comprise a rocker switch to receive input to operate the user interface mechanism between the first state, the second state, and the third state. In some such embodiments, in the first state, a first side of the rocker switch is parallel with a second side of the rocker switch, in the second state, the first side of the rocker switch is depressed, and in the third state, the second side of the rocker switch is depressed. In one or more embodiments, the user interface mechanism may include an interface member to receive rotational input to operate the user interface mechanism between the first state, the second state, and the third state. In one or more such embodiments, the user interface mechanism may comprise a cam to translate rotation of the interface member into linear motion. In many embodiments, the user interface mechanism may include a diaphragm switch to provide a mechanical resistance to linear motion of the balloon valve. In various such embodiments, the diaphragm switch inverts in response to linear motion of the balloon valve. In some such embodiments, the diaphragm switch biases the balloon valve into a position that corresponds to the first state. In several embodiments, the user interface mechanism may include a diaphragm switch to provide a mechanical resistance to linear motion of the working channel valve. In several such embodiments, the diaphragm switch biases the working channel valve into a position that corresponds to the first state. In various embodiments, the user interface mechanism may comprise a push-pull switch to receive input to operate the user interface mechanism between one or more of the first state, the second state, and the third state. In some embodiments, a transition from the first state to the second state produces tactile feedback via the user interface mechanism. In many embodiments, a transition from the second state to the third state produces tactile feedback via the user interface mechanism.

In another aspect, the present disclosure relates to a medical device, comprising an air/water valve set and a valve interface mechanism. The valve set may include a primary control valve, an air input valve, and an atmospheric valve. The primary control valve may be configured to control flow between a water input channel, a water output channel, and a balloon channel of a valve well, the air input valve may be configured to control flow through an air input channel of the valve well, and the atmospheric valve may be configured control flow through an atmospheric channel of the valve well. The valve interface mechanism may include a set of one or more biasing members and a user interface mechanism. The user interface mechanism may be operable between a first state, a second state, a third state, and a fourth state. The first state may comprise the valve set configured to place the air input channel in fluid communication with the atmospheric channel, the second state may comprise the valve set configured to place the air input channel in fluid communication with the air output channel, the third state may comprise the valve set configured to place the water input channel in fluid communication with the water output channel, and the fourth state may comprise the valve set configured to place the water input channel in fluid communication with the balloon channel. In the first state, the air input valve may permit flow through the air input channel and the atmospheric valve may permit flow through the atmospheric channel. In the second state, the air input valve may permit flow through the air input channel to the air output channel and the atmospheric valve may block flow through the atmospheric valve. In the third state, the primary control valve may permit flow from the water input channel to the water output channel, block flow through the balloon channel, and the air input valve may block flow through the air input channel. In the fourth state, the primary control valve may permit flow from the water input channel to the balloon channel, block flow through the water output channel, and the air input valve may block flow through the air input channel. In some embodiments, the user interface mechanism may comprise one or more of a lever, a rocker switch, and an interface member to receive input to operate the user interface mechanism to one or more of the first state, the second state, the third state, and the fourth state. In some such embodiments, the user interface mechanism may comprise the interface member to receive rotational input to operate the user interface mechanism between the first state, the second state, the third state, and the fourth state. In some further such embodiments, the user interface mechanism may comprise a cam to translate rotation of the interface member into linear motion. In various embodiments, the user interface mechanism may comprise a diaphragm switch to provide a mechanical resistance to linear motion of the balloon valve. In many embodiments, a transition from one or more of the first state to the second state, the second state to the third state, and the third state to the fourth state produces tactile feedback via the user interface mechanism.

In yet another aspect, the present disclosure relates to a method. The method may include placing a suction channel of a valve well in fluid communication with an atmospheric channel of the valve well based on operation of a user interface mechanism to a first state. The method may include, placing the suction channel of the valve well in fluid communication with a working channel of the valve well based on operation of the user interface mechanism to a second state. The method may include placing the suction channel of the valve well in fluid communication with a balloon channel of the valve well based on operation of the user interface mechanism to a third state. In some embodiments, the method may include rotating an interface member in a first direction to operate the user interface mechanism to the second state and rotating the interface member in a second direction to operate the user interface mechanism to the third state. In many embodiments, the method may include rotating the interface member adjust one or more valves in a suction valve set via a cam. In several embodiments, the method may include operating one or more of a lever, a rocker switch, and an interface member to adjust between one or more of the first state, the second state, and the third state.

In still another aspect, the present disclosure relates to a method. The method may include configuring a suction valve set to place a suction channel of a valve well in fluid communication with an atmospheric channel of the valve well based on operation of a user interface mechanism to a first state. The method may include configuring the suction valve set to place the suction channel of the valve well in fluid communication with a working channel of the valve well based on operation of the user interface mechanism to a second state. The method may include configuring the suction valve set to place the suction channel of the valve well in fluid communication with a balloon channel of the valve well based on operation of the user interface mechanism to a third state. In some embodiments, the method may include rotating an interface member in a first direction to operate the user interface mechanism to the second state and rotating the interface member in a second direction to operate the user interface mechanism to the third state. In some such embodiments, the method may include translating the rotation of the interface member into a linear motion of one or more valves in the suction valve set via a cam. In various embodiments, the method may include producing tactile feedback via the user interface mechanism in response to operation of the user interface mechanism to one or more of the first state, the second state, and the third state. In several embodiments, the user interface mechanism may comprise one or more of a lever, a rocker switch, and an interface member to receive input to operate the user interface mechanism to one or more of the first state, the second state, and the third state.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 includes a block diagram of an exemplary suction valve assembly, according to one or more embodiments described herein.

FIG. 2 includes a block diagram of an exemplary air/water (AW) valve assembly, according to one or more embodiments described herein.

DETAILED DESCRIPTION

Figure 3A:
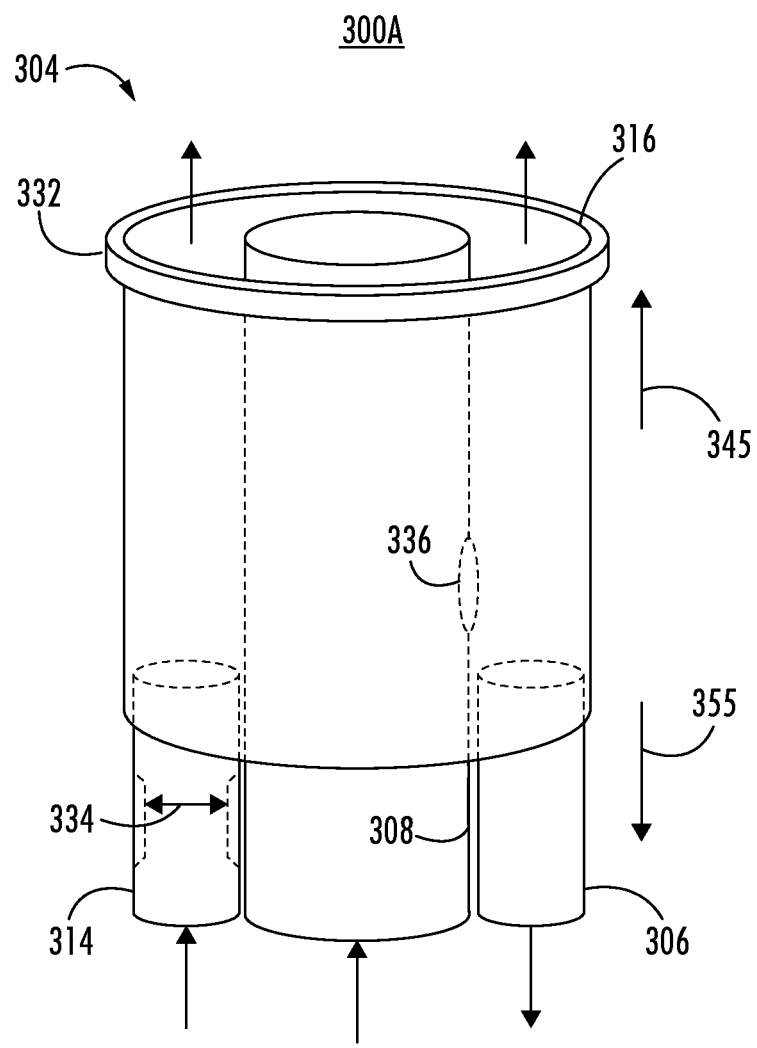
FIGS. 3A-3D illustrate various aspects of an exemplary suction valve well, according to one or more embodiments described herein.

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable. These and other embodiments are described and claimed.

Some challenges when controlling the flow of fluids through endoscopes include unreliable valves prone to failure. For example, many valves and valve interface mechanisms are fragile and likely to leak. These issues can be compounded when the components are designed, constructed, and/or assembled economically to facilitate disposal after a single use. Alternatively, these issues can be compounded when reusable components are worn down from multiple use/cleaning cycles. Adding further complexity, user interface mechanisms may be confusing to operate and require a steep learning curve. For instance, delicate and nonintuitive movements may be required to accurately control fluid flows. Further, little or no feedback may be provided to indicate how a set of valves is arranged. For example, an operator may not be able to easily discern via a user interface mechanism whether the set of valves is arranged to provide suction to a working channel or provide suction to a balloon channel. These and other factors may result in devices, systems, and methods for controlling the flow of fluids through endoscopes that are difficult to use, inaccurate, inefficient, and/or unreliable, resulting in limited applicability and/or uncertain outcomes. Such limitations can drastically reduce the dependability, ergonomics, and intuitiveness of flow control in endoscopes and procedures performed therewith, contributing to reduced usability, adverse outcomes, excess fatigue, and/or lost revenues.

Various embodiments described herein include one or more components of a valve assembly, such as valves and/or valve interface mechanisms, that provide reliable and intuitive control of fluid flow through endoscopes. In several embodiments, the components may provide reliable operation while providing sufficient value to be disposable (e.g., single-use). In many embodiments, the components may provide accurate and intuitive interfaces to improve operator experience. For example, embodiments may utilize one or more of up-and-down, forward-and-back, side-to-side, and rotational interfaces to provide ergonomic and intuitive control of fluid flows through endoscopes. Some such embodiments may include one or more interface members, such as push/pull switches, bellows, rotational switches, knobs, buttons, and toggle switches. In many embodiments, one or more of the components may provide/enable tactile feedback. For example, one or more components of the valve interface mechanism may provide tactile or haptic feedback to indicate how a set of valves is arranged (e.g., arranged to permit/block flows between various channels). In some examples, the force to operate a user interface mechanism may vary to indicate transitions between valve states. In various embodiments, tactile feedback may be produced as a result of different components of a valve assembly coming into contact, such as due to received input.

In various embodiments, one or more of the components may be designed to simplify manufacturability. For instance, the location of one or more biasing members may simplify component assembly. In these and other ways, components/techniques described here may improve operator experience, decrease learning curves, improve reliability, and/or decrease manufacturing complexity via realization of more efficient and valuable devices, systems, and methods for controlling the flow of fluids in endoscopic systems. In many embodiments, one or more of the advantageous features may result in several technical effects and advantages over conventional technology, including increased capabilities and improved adaptability.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to specific medical devices and systems (e.g., an endoscope), it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures, Endoscopic Retrograde Cholangio-Pancreatography (ERCP) procedures, and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional/operator when introducing a device into a patient, while the term "proximal" refers to the end closest to the medical professional when introducing a device into a patient.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may provide reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked, and/or the flow of water may be controlled from water input channel 208 to one of water output channel 212, the balloon channel 214, or blocked.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to provide medium to facilitate transmission of sound waves and capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214. In other embodiments, one or more of the components of the valve assembly for AW and/or suction may be implemented in configurations that do not require or include a balloon, such as video capable scope with ultrasound functionality.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a lever, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa, without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve well block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Figure 3B:
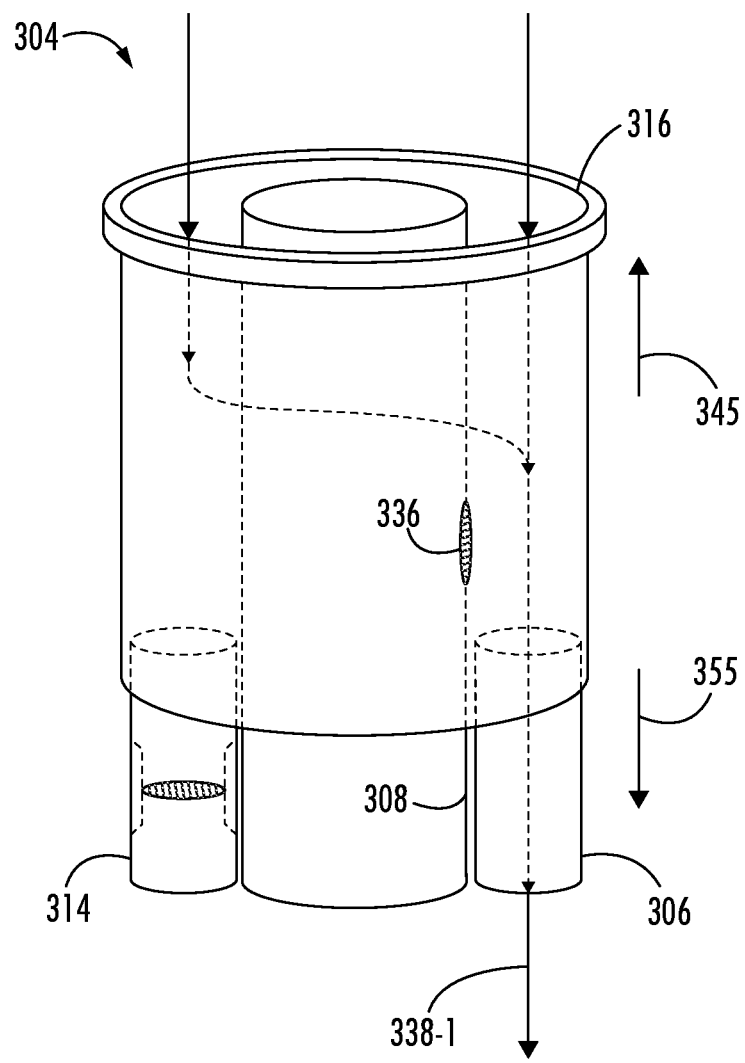

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. For example, suction channel 306 may be an input in the handle of a medical scope that is connected to a vacuum system, such as for a hospital, home, and/or mobile device.

Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Figure 3C:
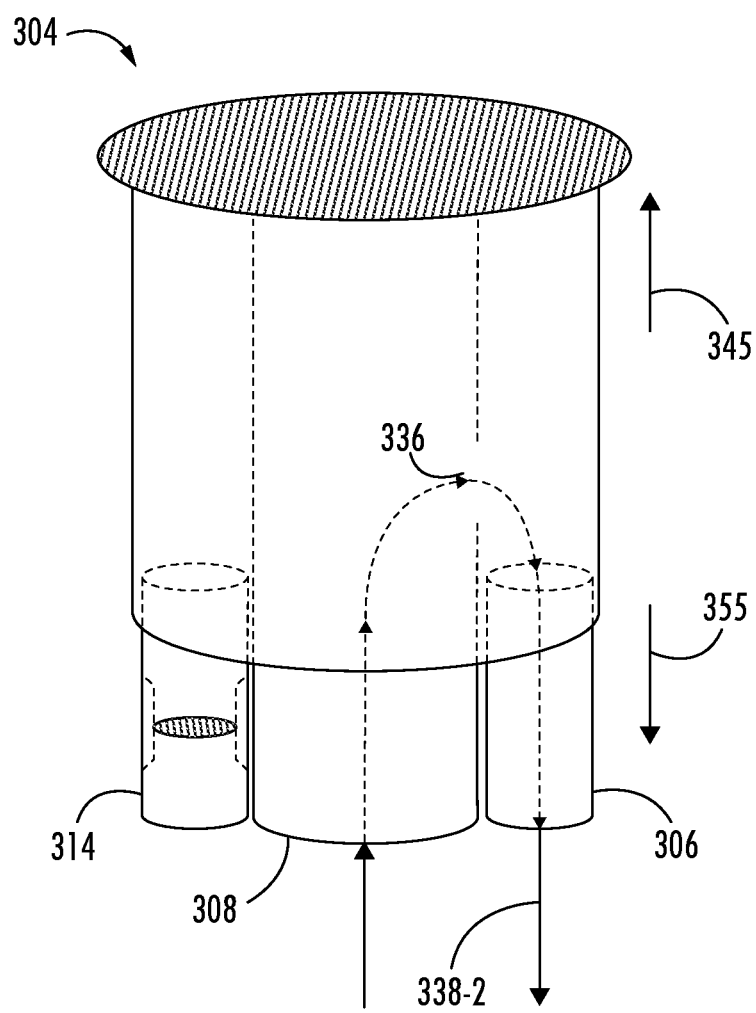

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Figure 3D:
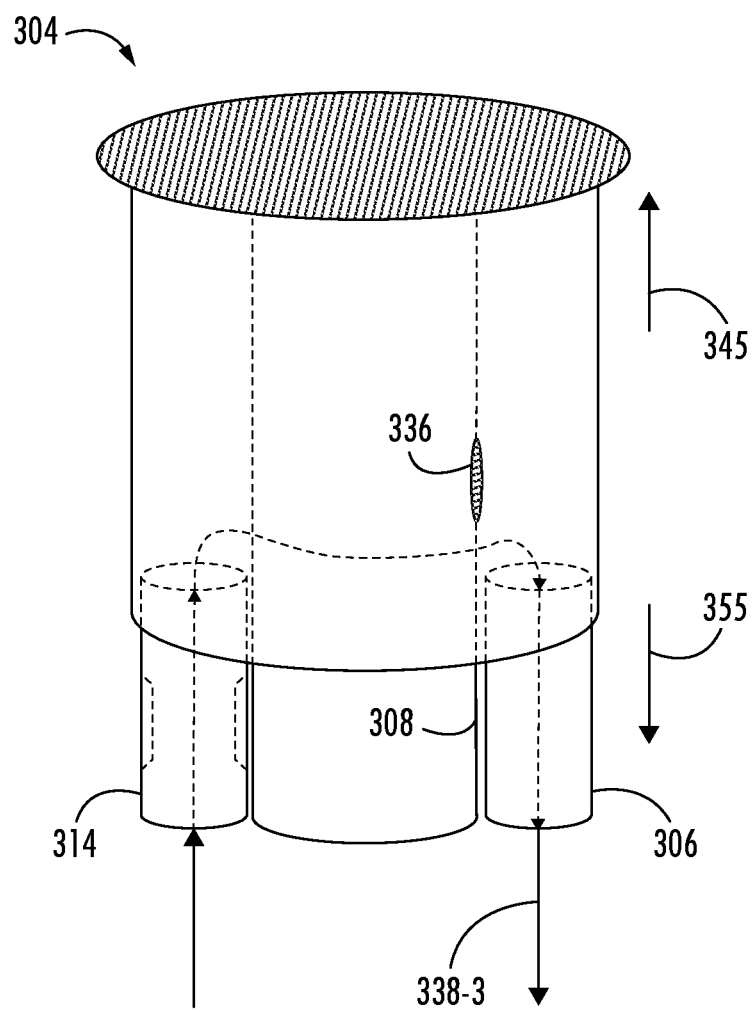

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Figure 4A:
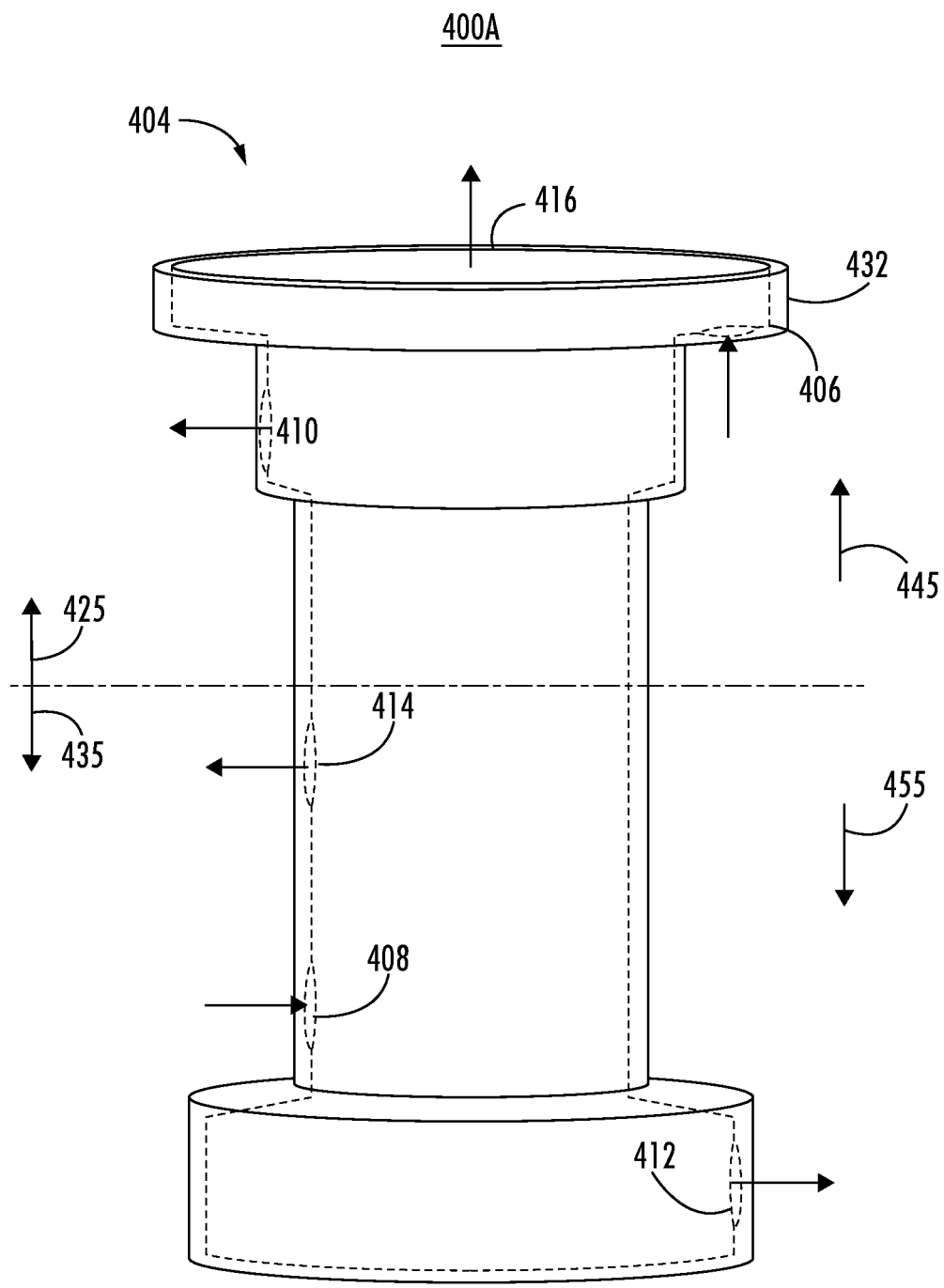
FIGS. 4A-4E illustrate various aspects of an exemplary AW valve well, according to one or more embodiments described herein.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Figure 4B:
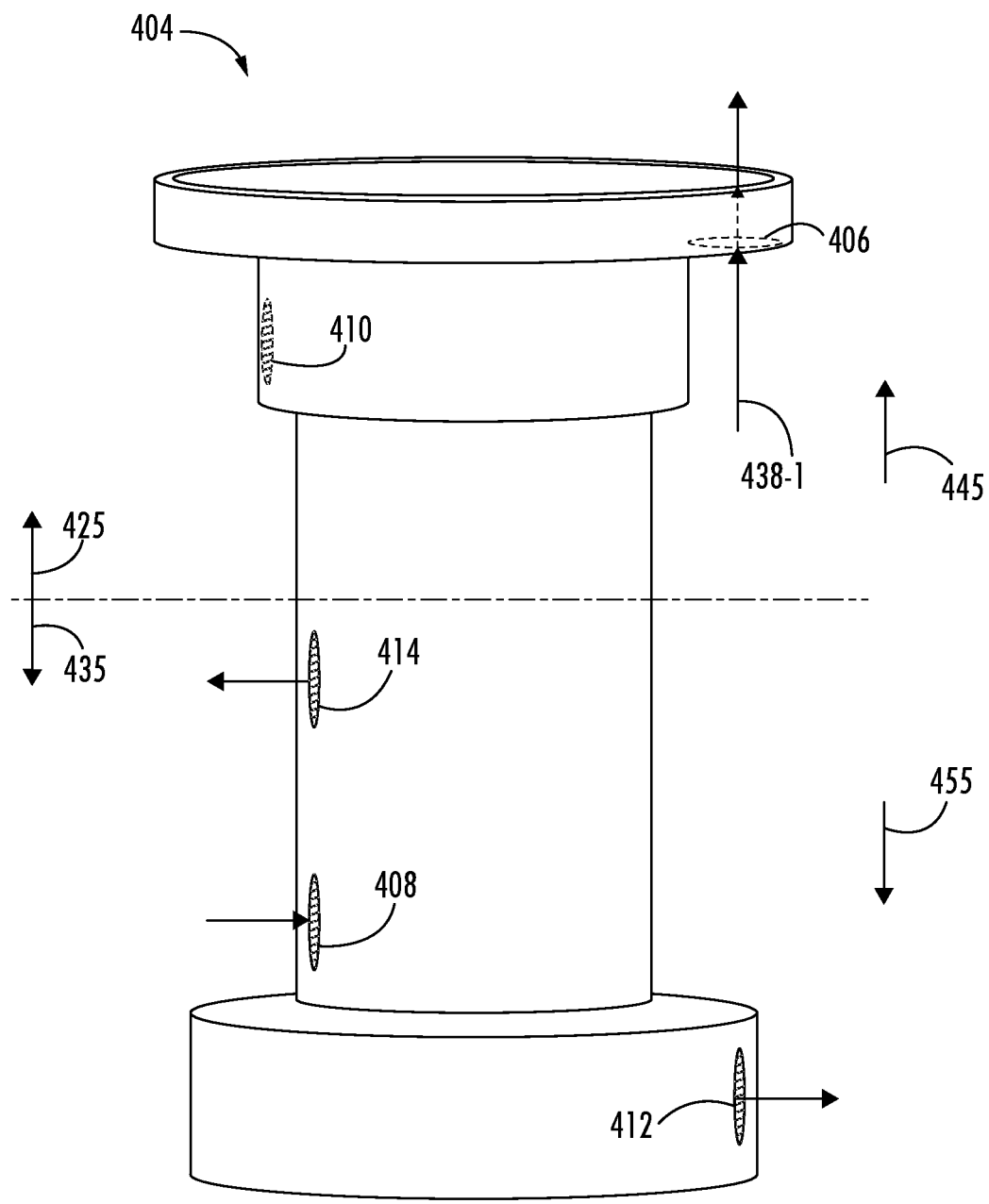

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Figure 4C:
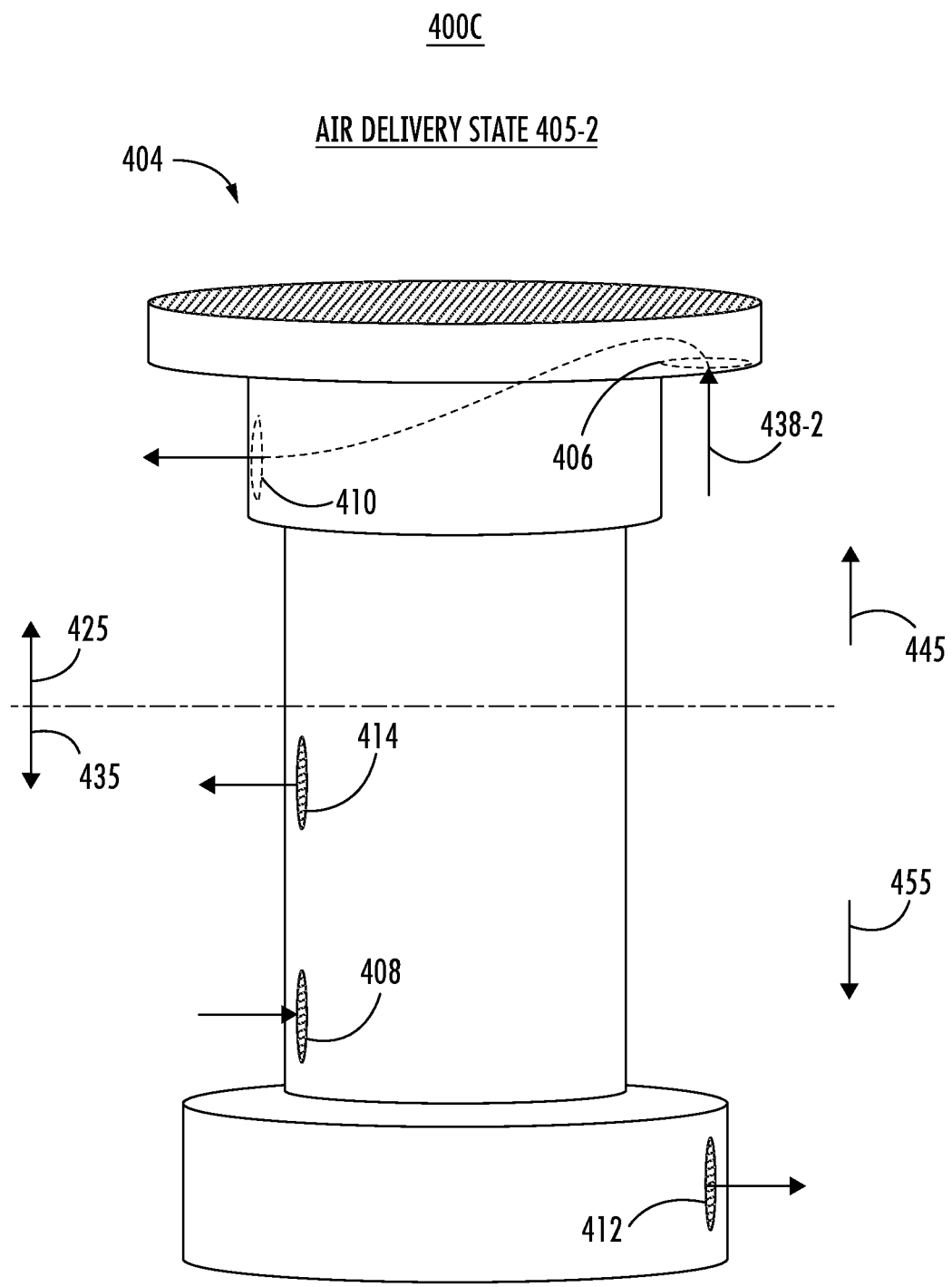

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Figure 4D:
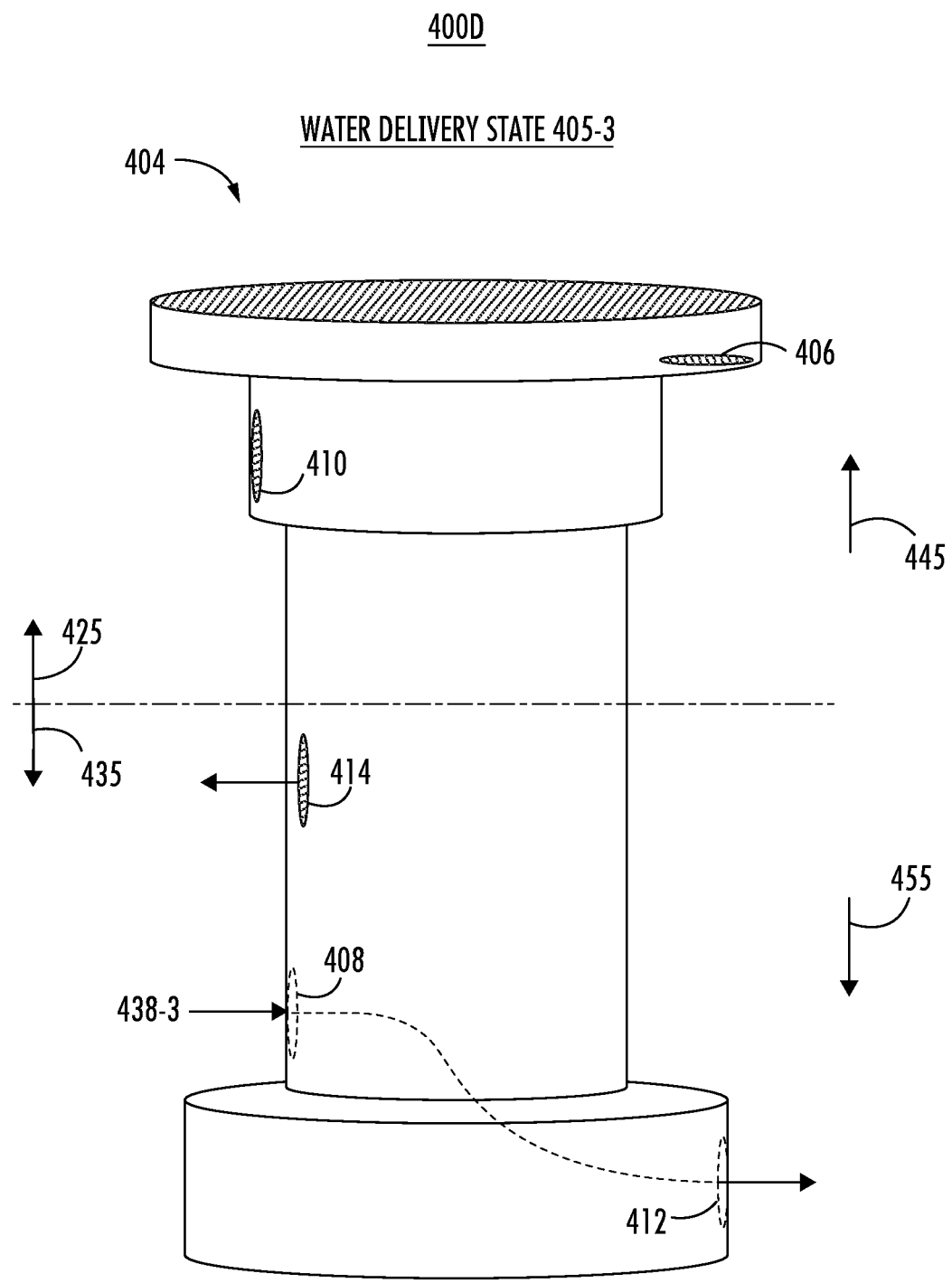

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Figure 4E:
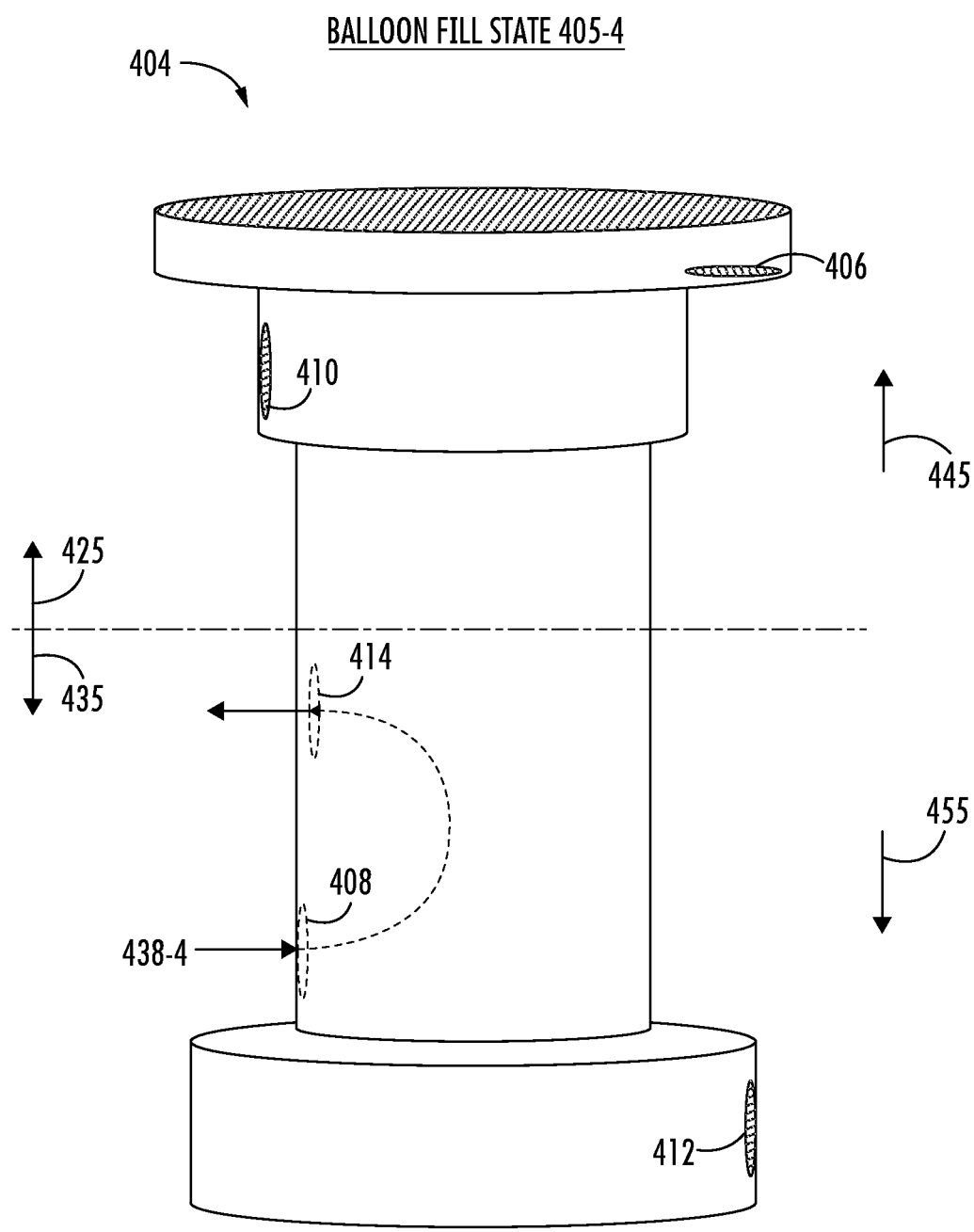

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Figure 5:
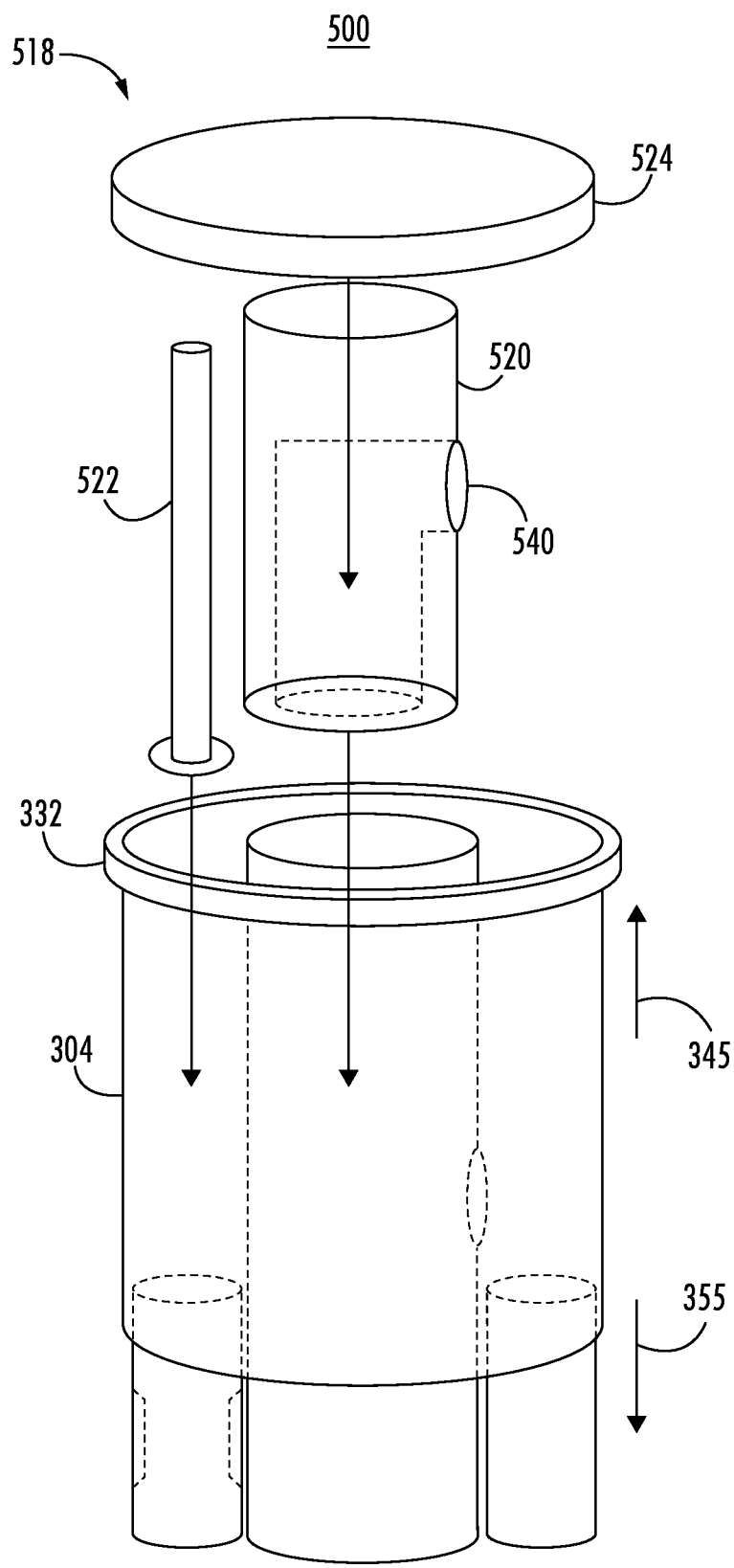
FIG. 5 illustrates an exemplary suction valve set, according to one or more embodiments described herein.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel 314 of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Figure 6A:
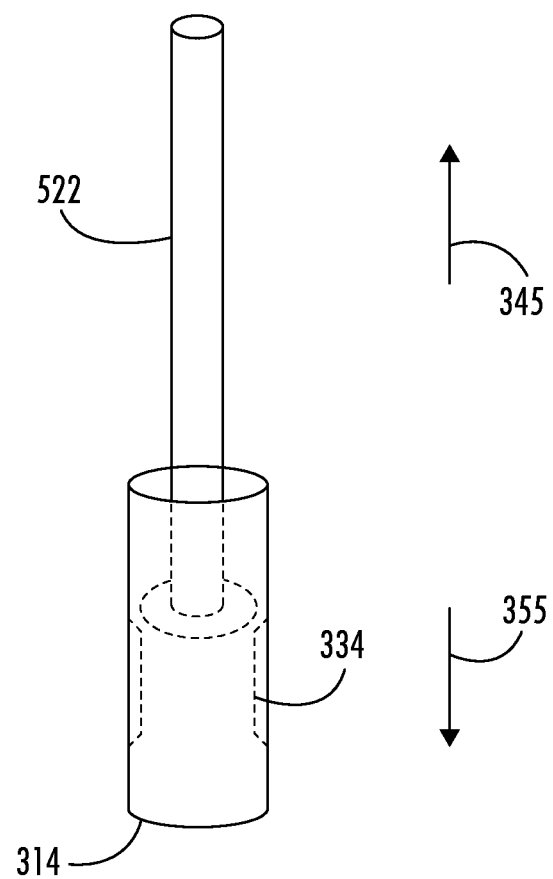
FIGS. 6A-8C illustrate various aspects of exemplary valves in suction valve sets, according to one or more embodiments described herein.
Figure 6B:
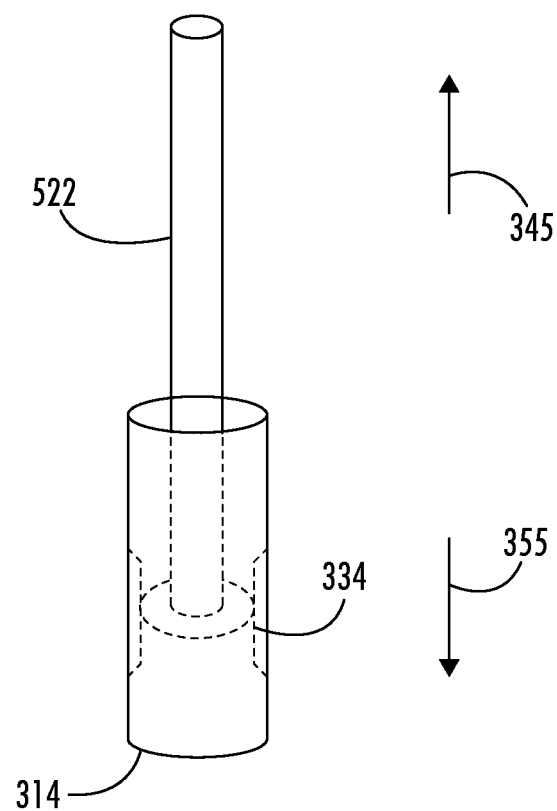

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Figure 7A:
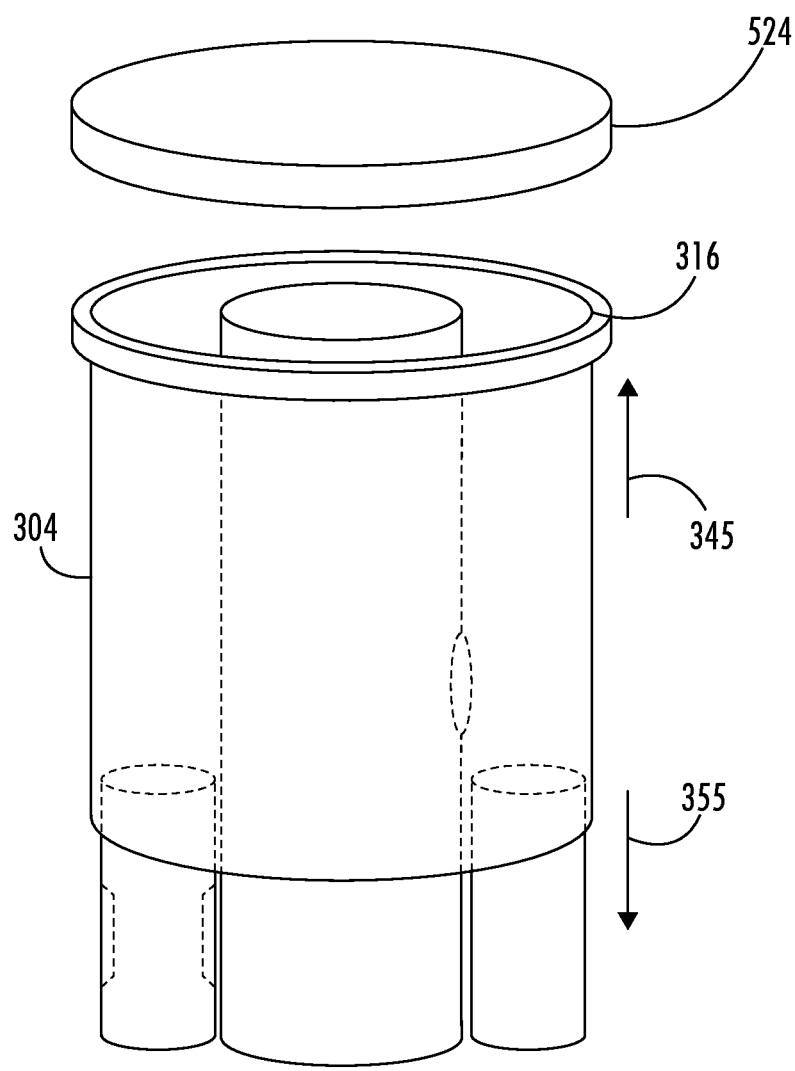
Figure 7B:
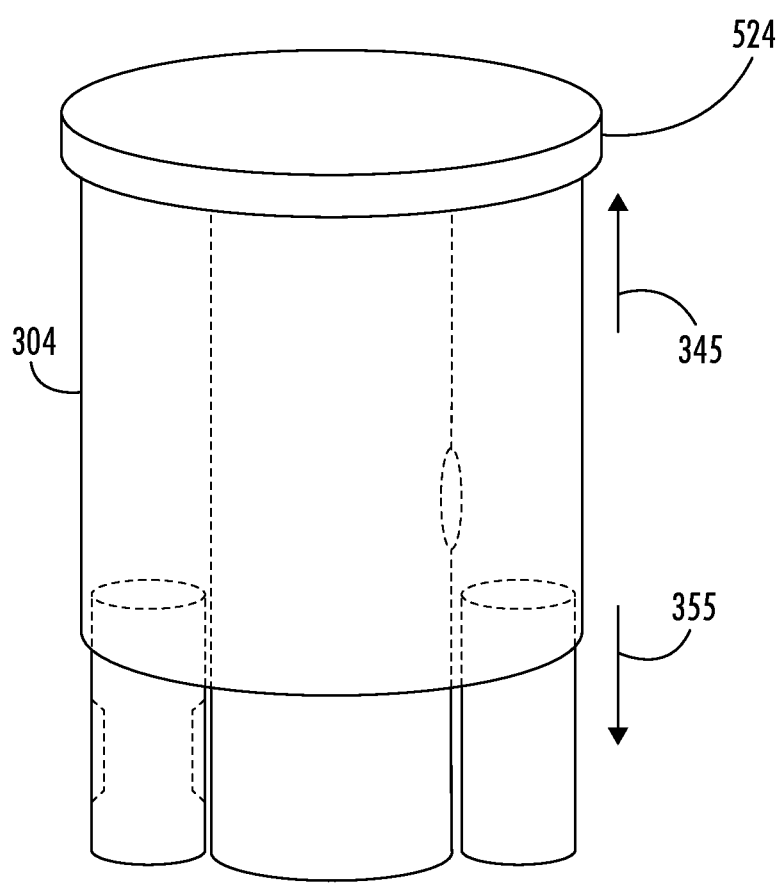

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Figure 8A:
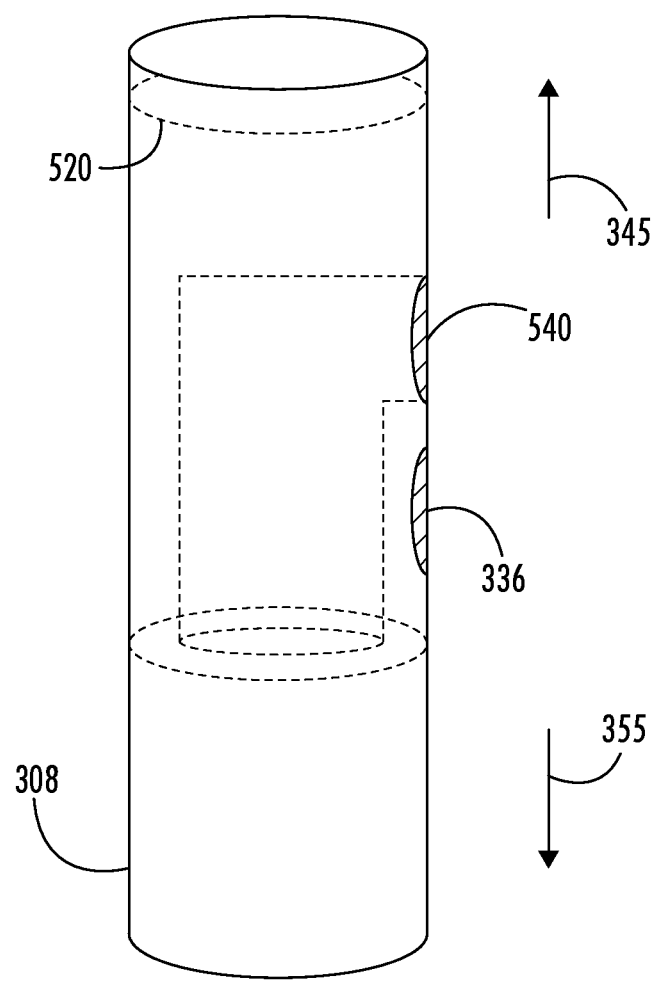
Figure 8B:
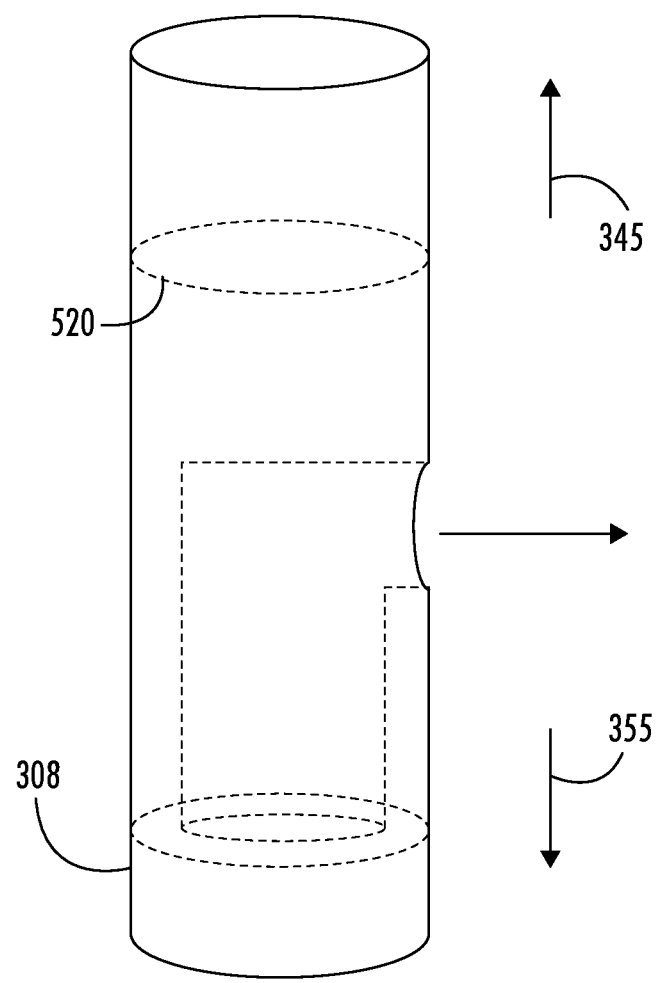
Figure 8C:
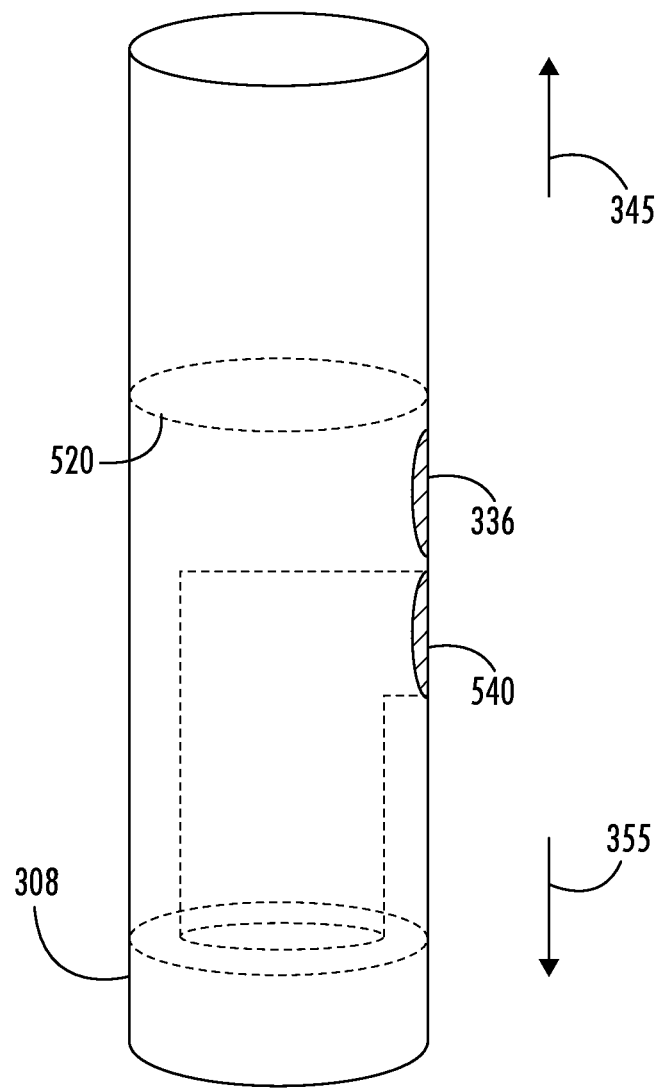

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit suction flow through working channel 308. For example, the flow may enter through the bottom of the working channel valve 520 and exit through the well radial hole 336. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel radial hole 440 is below well radial hole 336.

Figure 9:
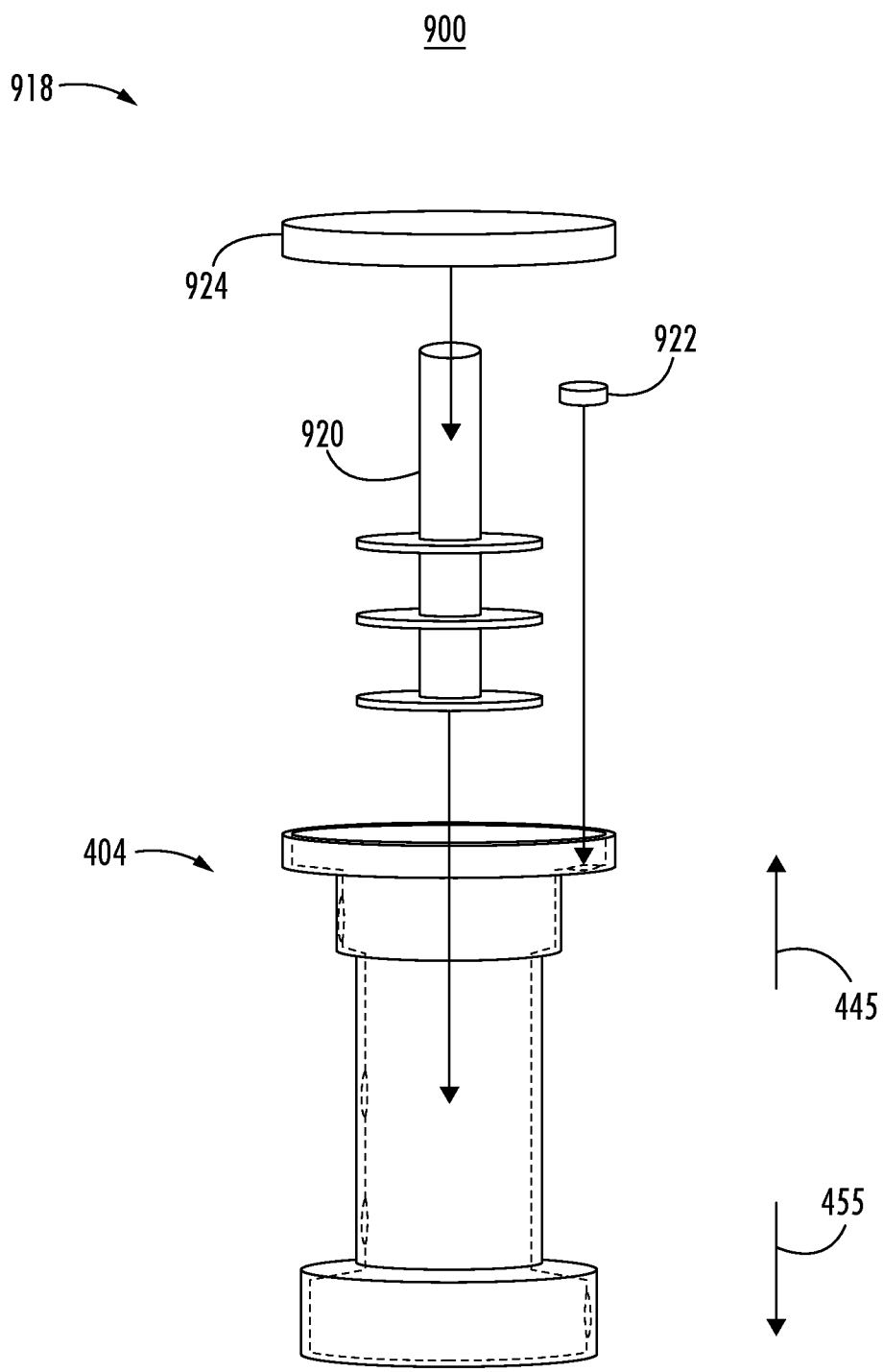
FIG. 9 illustrates an exemplary AW valve set, according to one or more embodiments described herein.

Referring to FIG. 9, environment 900 illustrates AW valve set 918 in conjunction with AW valve well 404. AW valve set 918 may include primary control valve 920, air input valve 922, and atmospheric valve 924. In several embodiments, the primary control valve 920 may be inserted into the AW valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

Figure 10A:
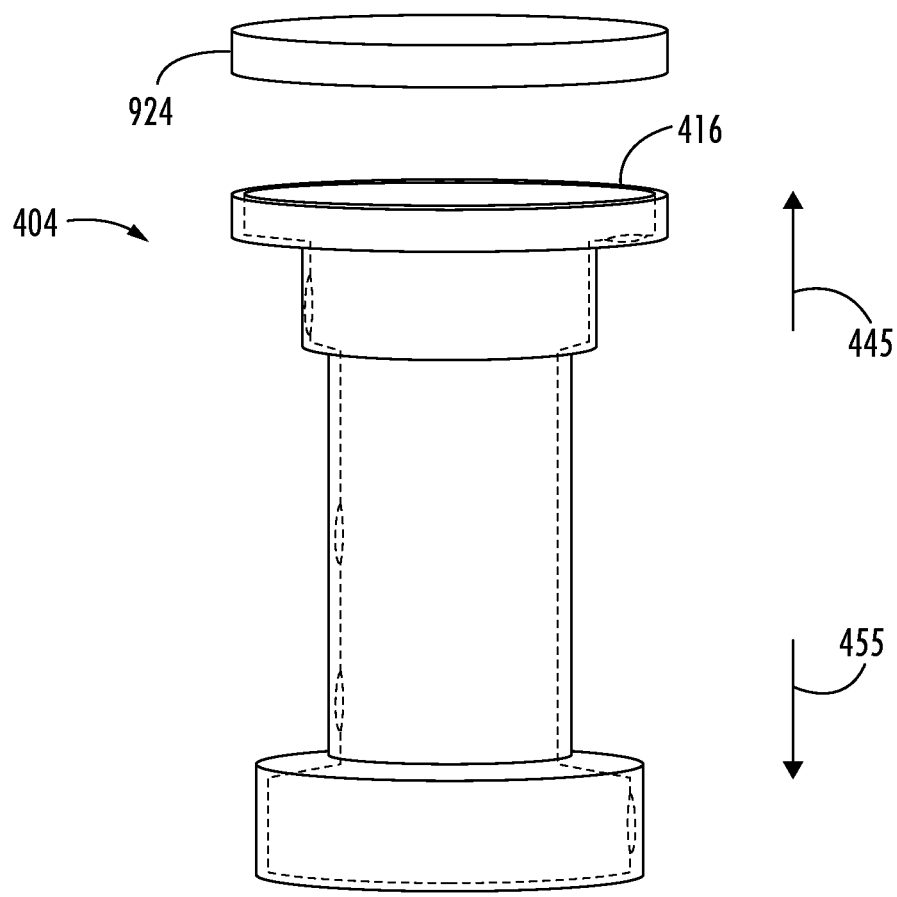
FIGS. 10A-12C illustrate various aspects of exemplary valves in AW valve sets, according to one or more embodiments described herein.
Figure 10B:
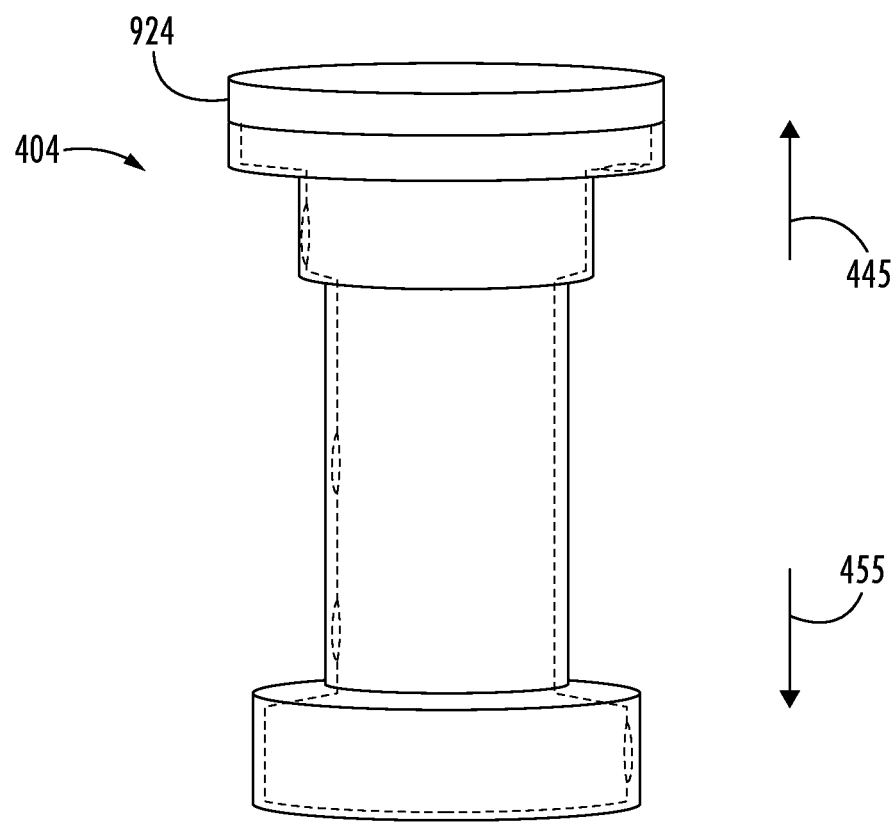

Referring to FIG. 10A, environment 1000A illustrates an atmospheric valve open state. In the atmospheric valve open state, the atmospheric valve 924 may allow flow through the atmospheric channel of AW valve well 404. Referring to FIG. 10B, environment 1000B illustrates an atmospheric valve sealed state 1015-2. In the atmospheric valve sealed state 1015-2, the atmospheric valve 924 may prevent flow through atmospheric channel of AW valve well 404. As will be discussed in more detail below, in operation, fluid communication with the atmosphere may be provided through a passage/channel in, or created by, one or more components (e.g., primary control valve 920). Further, one or more components may be used to seal portions of the atmospheric channel 316 to facilitate control of fluid communication with the atmosphere by atmospheric valve 924. In some embodiments, atmospheric valve 924 may include a plurality of components configured to control fluid communication with the atmosphere.

Figure 11A:
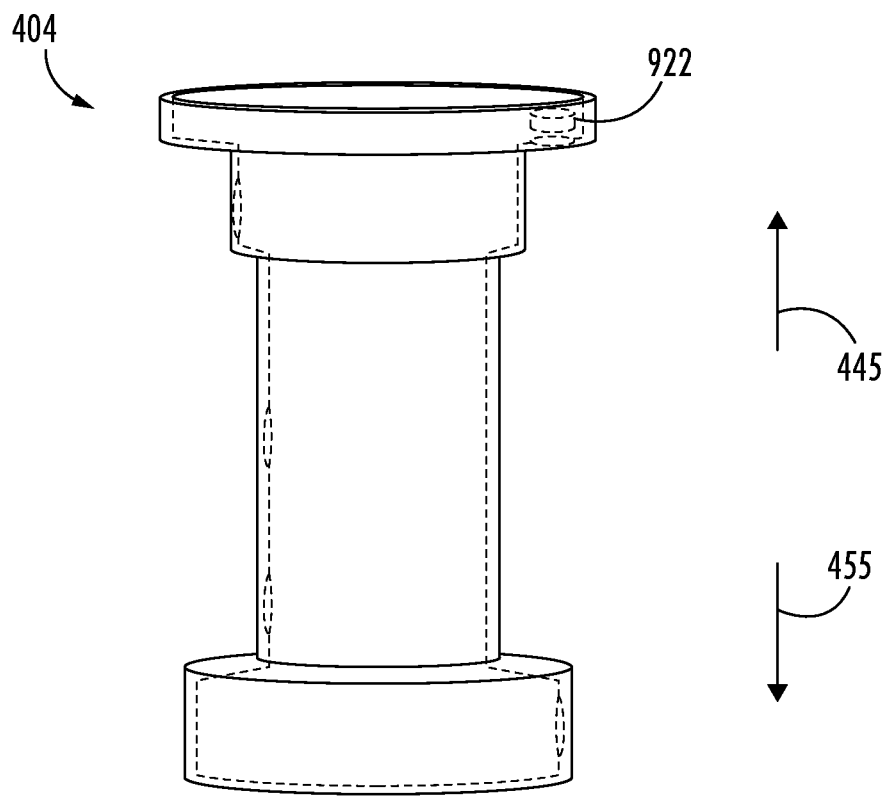
Figure 11B:
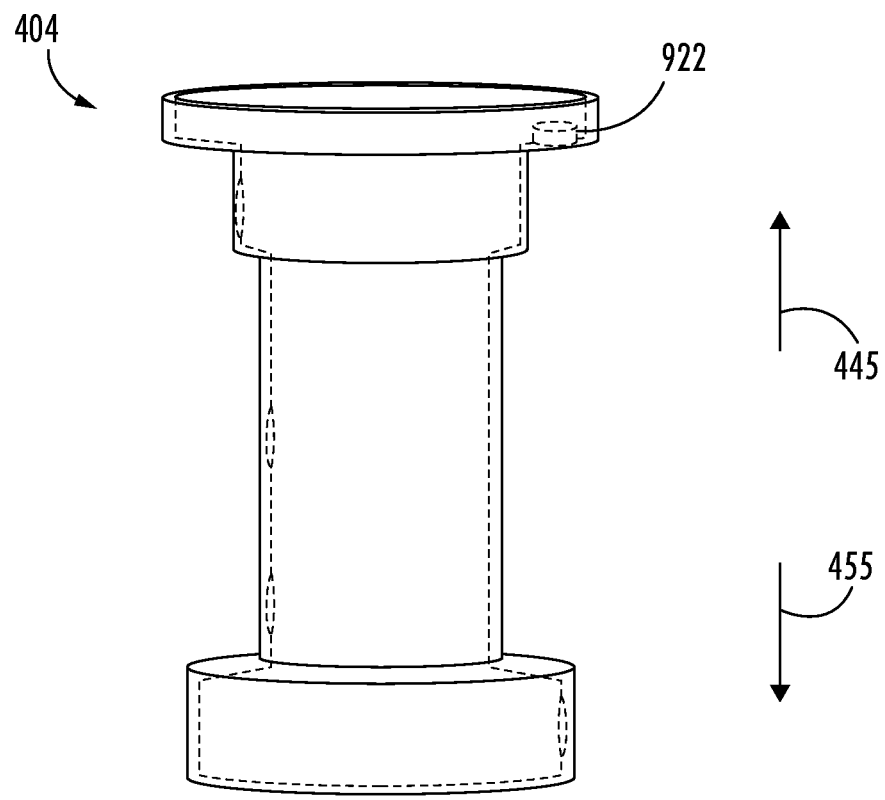

Referring to FIG. 11A, environment 1100A illustrates an air input valve open state 1115-1. In the air input valve open state 1115-1, the air input valve 522 may allow flow through the air input channel of AW valve well 404. Referring to FIG. 11B, environment 1100B illustrates an air input valve sealed state 1115-2. In the air input valve sealed state 1115-2, the air input valve 922 may prevent flow through the air input channel of AW valve well 404. In some embodiments, sealing the air input channel may cause a fluid source (e.g., water reservoir) to be pressurized, thereby enabling/causing fluid to flow into the AW valve well 404 via water input channel 408.

Figure 12A:
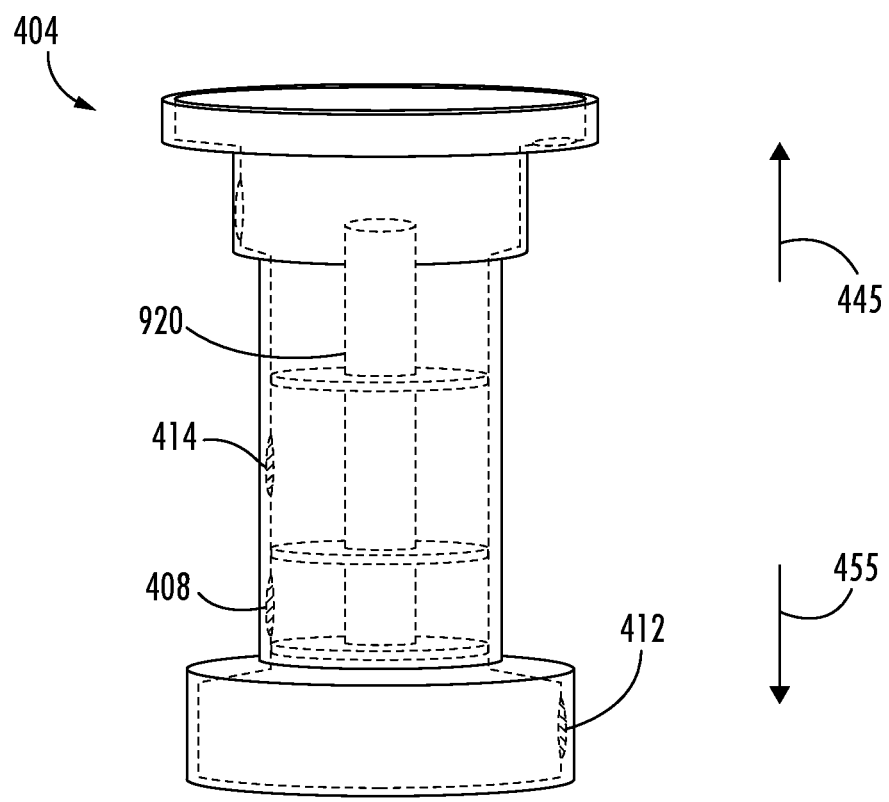
Figure 12B:
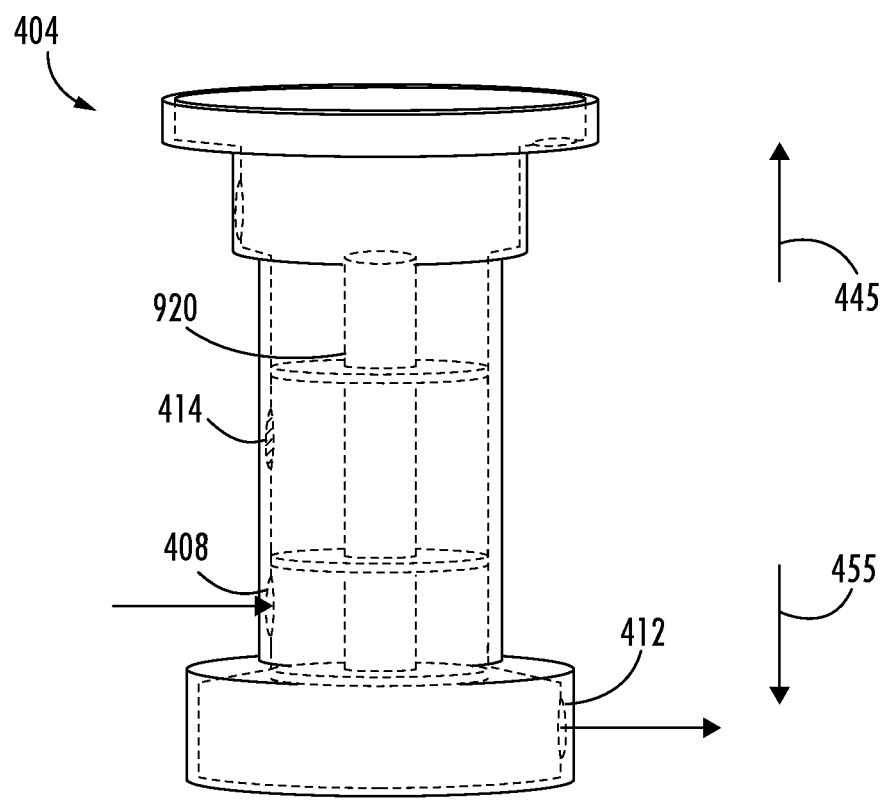
Figure 12C:
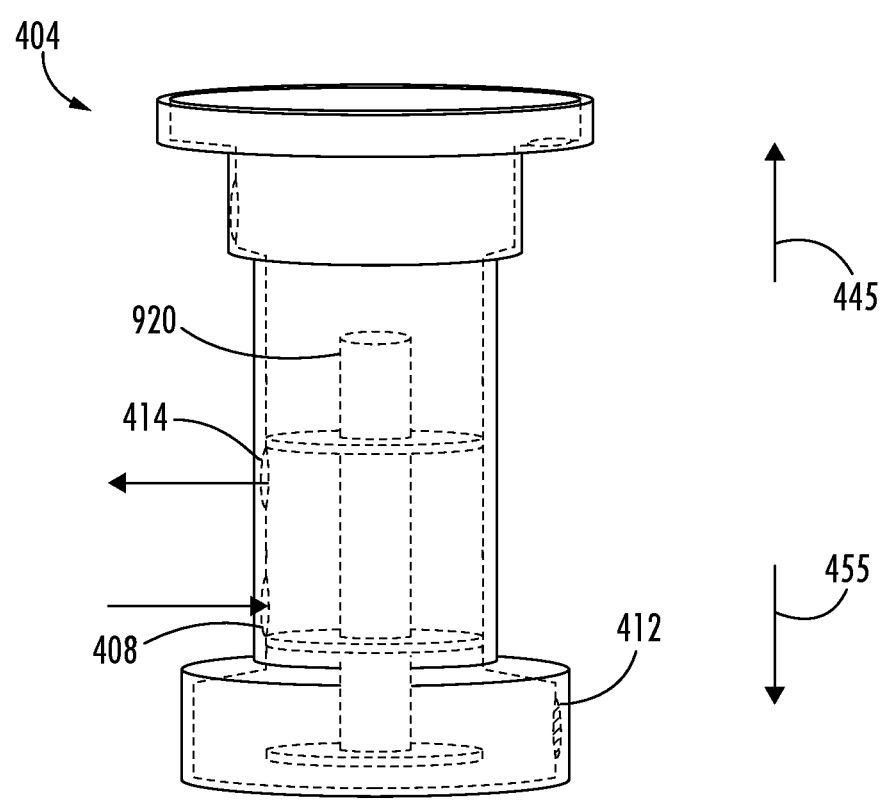

Referring to FIG. 12A, environment 1200A illustrates a primary valve sealed state 1215-1. In the primary valve sealed state 1215-1, the primary control valve 920 may prevent flow through one or more of the balloon channel 414, water input channel 408, and water output channel 412. Referring to FIG. 12B, environment 1200B illustrates a primary valve water output state 1215-2. In the primary valve water output state 1215-2, the primary control valve 920 may be positioned to block flow through balloon channel 414 and permit flow from water input channel 408 to water output channel 412. In various embodiments, primary control valve 920 may utilize changes in diameter in AW valve well 404 to control flow. Referring to FIG. 12C, environment 1200C illustrates a primary valve balloon fill state 1215-3. In the primary valve balloon fill state 1215-3, the primary control valve 920 may be positioned to block flow through water output channel 412 and permit flow from water input channel 408 to balloon channel 414. In various embodiments, one or more features of primary control valve 920 may operate as valves for multiple channels. In some embodiments, one or more features of primary control valve 920 may comprise one or more channels, or one or more portions thereof. For example, primary control valve 920 may comprise atmospheric channel 416.

Figure 13A:
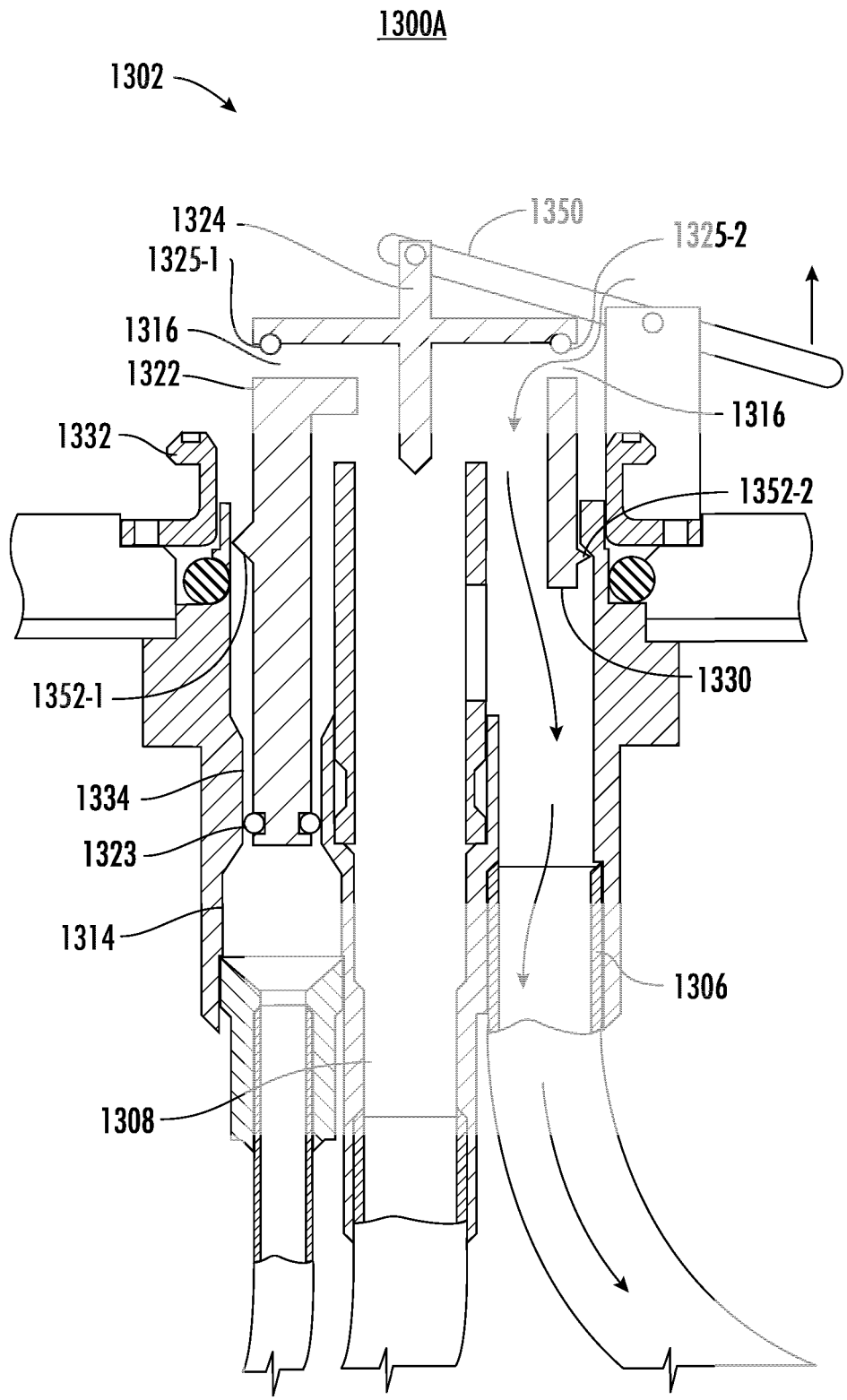
FIGS. 13A-13C illustrate various aspects of an exemplary suction valve assembly, according to one or more embodiments described herein.
Figure 13B:
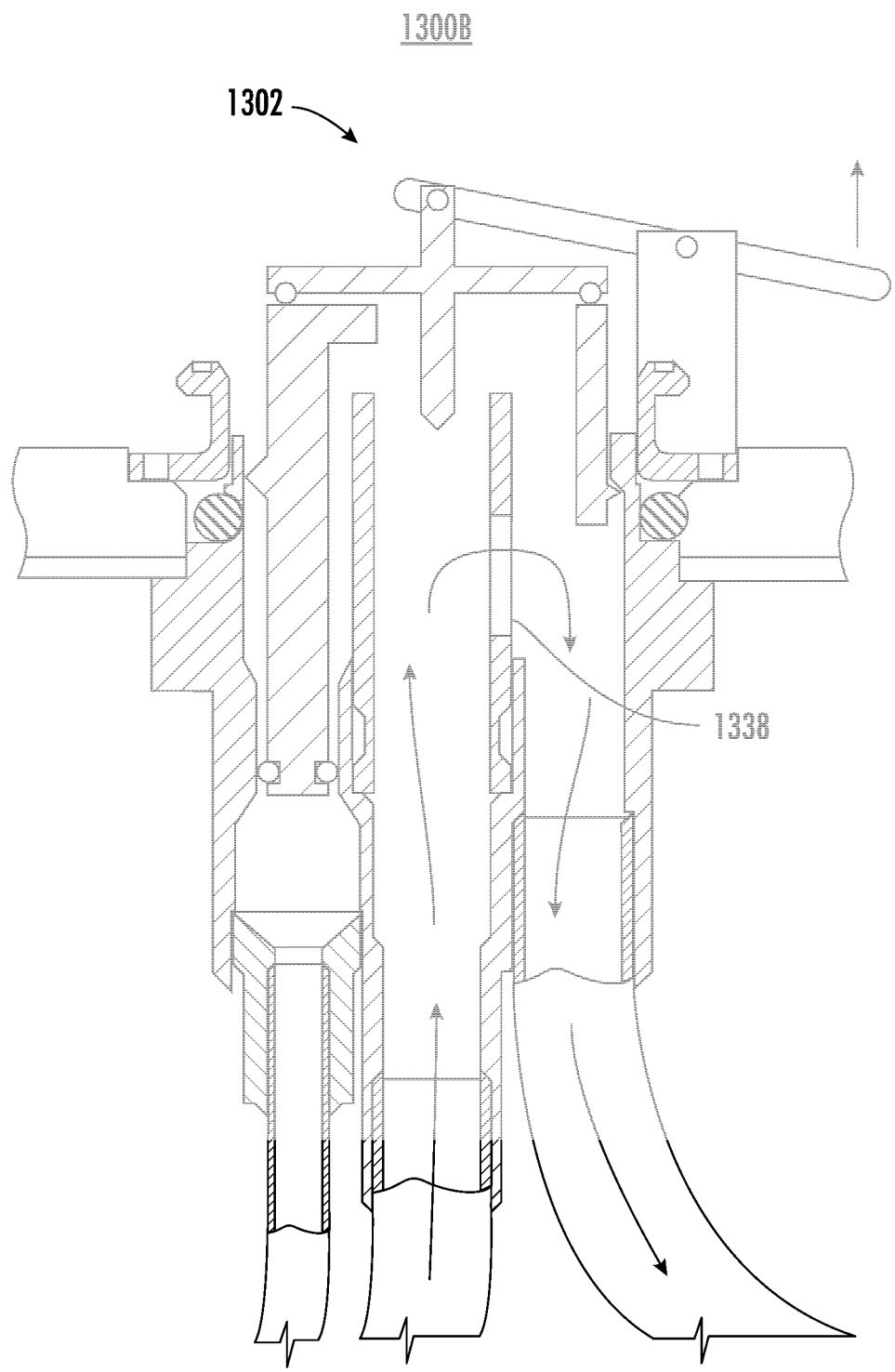
Figure 13C:
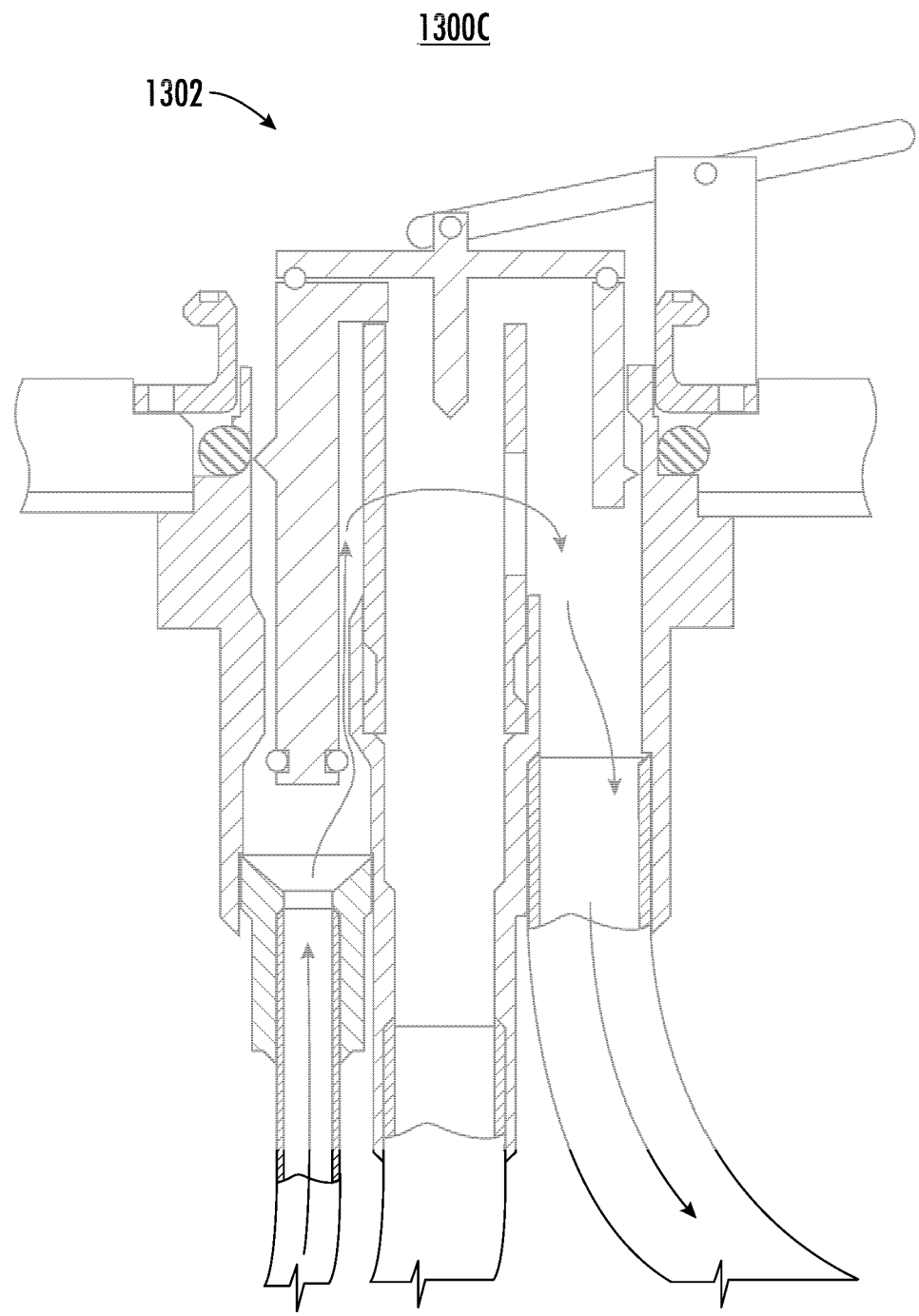

FIGS. 13A-13C illustrate various aspects of an exemplary suction valve assembly 1302 in environments 1300A-C, according to one or more embodiments described herein. In many embodiments, a cross section of one or more portions and/or components may be illustrated in environments 1300A-C. In some embodiments, one or more components of FIGS. 13A-13C may be the same or similar to one or more other components described herein. Suction valve assembly 1302 includes atmospheric valve 1324, atmospheric seals 1325-1, 1325-2, balloon valve 1322, balloon valve seal 1323, linkage 1330, lip 1332, valve seals 1352-1, 1352-3, necking portion 1334, balloon channel 1314, working channel 1308, lever 1350, atmospheric channel 1316, and suction channel 1306. Environment 1300A may illustrate the suction valve assembly 1302 in a first position, environment 1300B may illustrate the suction valve assembly 1302 in a second position, and environment 1300C may illustrate the suction valve assembly 1302 in a third position. Embodiments are not limited in this context.

The illustrated embodiments of the suction valve assembly 1302 may utilize a lever mechanism to drive down suction valves for the balloon and working channels. In many embodiments the lever 1350 may comprise an interface member. The first position may include an open position, allowing for air to flow into the suction channel from the atmosphere (see FIG. 13A). Additionally, the balloon valve seal 1323 may seal against the necking portion 1334 in the first position. In various embodiments, the first position may be the same or similar to one or more of atmospheric suction state 305-1, balloon valve sealed state 615-2, atmospheric valve open state 715-1, and working channel valve first sealed state 815-1.

As the lever is articulated, depending on lever position, valves and/or valve interface mechanisms may be transitioned to the second position. The second position may seal off suction to the atmosphere thereby forcing a vacuum to cause flow through the working channel (see FIG. 13B). Additionally, the balloon valve seal 1323 may seal against the necking portion 1334 in the first position. In many embodiments, the second position may be the same or similar to one or more of working channel suction state 305-2, balloon valve sealed state 615-2, atmospheric valve sealed state 715-2, and working channel valve open state 815-2. In the second position, atmospheric seal 1325-1 may seal against the upper portion of balloon valve 1322 and atmospheric seal 1325-2 may seal against the upper portion of linkage 1330. In many embodiments, atmospheric seals 1325-1, 1325-2 may be part of a single seal, such as an O-ring.

In various embodiments, if the lever is released one or more biasing members (e.g., a tension, torsion, and/or compression spring), based on positioning of the one or more biasing members, may force a user interface mechanism and/or one or more valves back to an original position (e.g., the first position). In some embodiments, in the third position, a hard stop may be advanced to move the balloon valve and open the balloon channel.

The third position may seal off suction to the atmosphere and to the working channel thereby forcing a vacuum to cause flow through the balloon channel (see FIG. 13C). In many embodiments, the third position may be the same or similar to one or more of working channel suction state 305-3, balloon valve open state 615-1, atmospheric valve sealed state 715-2, and working channel valve second sealed state 815-3. In many embodiments, the third position may include, or utilize, an internal spring mechanism.

Accordingly, in one or more embodiments, moving from the first to the second position may provide an amount of mechanical feedback that can be distinguished from an amount of mechanical feedback provided when moving from the second to the third position. In many embodiments, this feedback may provide an indication to operators exactly what they are state they are accessing while utilizing the lever. In another embodiment, there may be little or no resistance to moving from the first position to the second position and an external spring may provide resistance when moving from the second to third positions.

Figure 14:
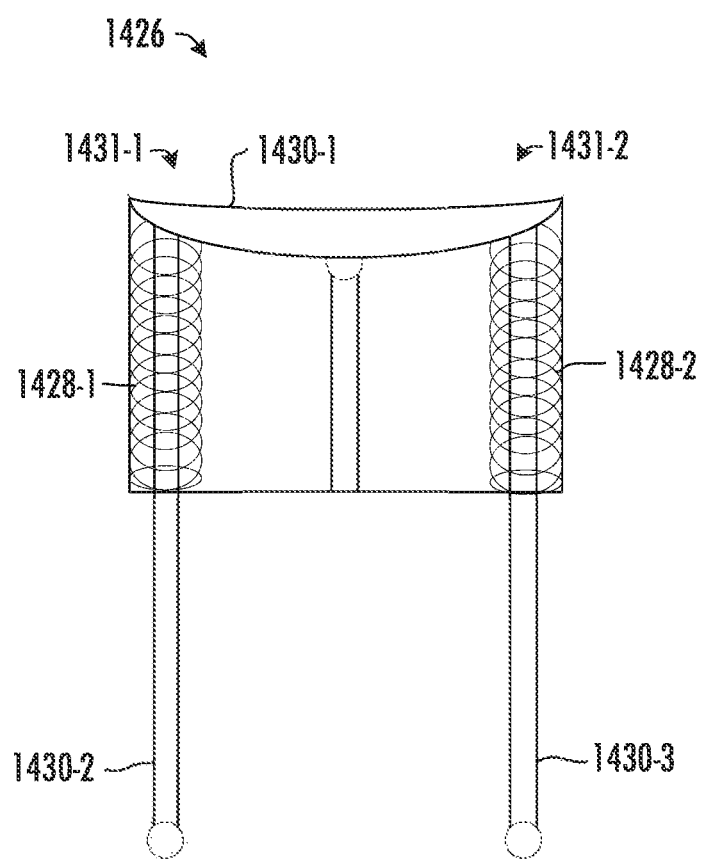
FIG. 14 illustrates an exemplary valve interface mechanism, according to one or more embodiments described herein.

FIG. 14 illustrates various aspects of an exemplary valve interface mechanism 1426 in environment 1400, according to one or more embodiments described herein. In many embodiments, a cross section of one or more portions and/or components may be illustrated in environment 1400. In some embodiments, one or more components of FIG. 14 may be the same or similar to one or more other components described herein. Valve interface mechanism 1426 may have a biasing member set comprising biasing members 1428-1, 1428-2 (e.g., springs) and a user interface mechanism comprising rocker switch 1430-1 with a first side 1431-1 and a second side 1431-2, and valve linkages 1430-2, 1430-3. Embodiments are not limited in this context.

As opposed, or in addition, to using input comprising two positions of motion in the same plane (e.g., up and down) for controlling flow, valve interface mechanism 1426 may utilize side-to-side motion to toggle between states/arrangements/functions. In various embodiments, to an operator, the valve interface mechanism 1426 may look like a rounded switch. In many embodiments, the valve interface mechanism 1426 may provide an ergonomic and comfortable rest of an operator's finger when in various positions.

In some embodiments, in the first position, the first and second sides 1431-1, 1431-2 may be level. In some such embodiments, biasing members 1428-1, 1428-2 may maintain the rocker switch 1430-1 in the first position when no input is being received. In several embodiments, depressing the first side 1431-1 of the rocker switch 1430-1 may cause a transition in a corresponding valve assembly from the first position to the second position. In many embodiments, depressing the second side 1431-2 of the rocker switch 1430-1 may transition the corresponding valve assembly from the first position to the third position.

Figure 15A:
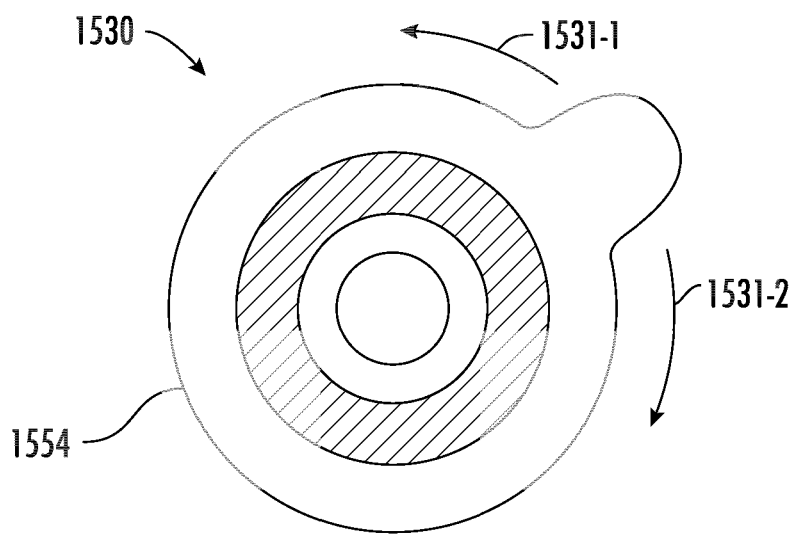
FIGS. 15A and 15B illustrate various aspects of an exemplary user interface mechanism, according to one or more embodiments described herein.
Figure 15B:
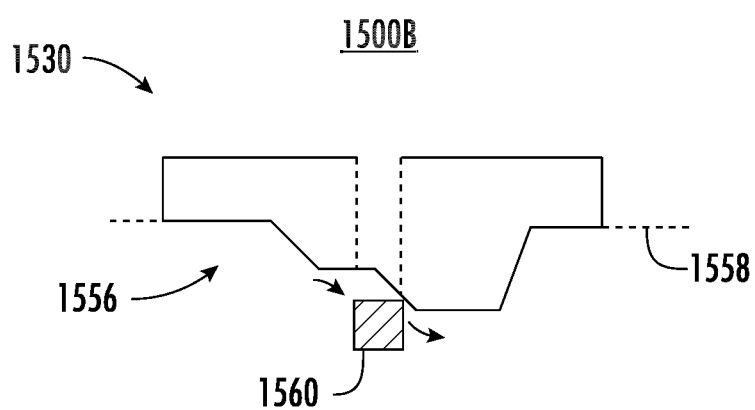

FIGS. 15A and 15B illustrate various aspects of an exemplary user interface mechanism 1530 in environments 1500A, 1500B, according to one or more embodiments described herein. In many embodiments, a cross section of one or more portions and/or components may be illustrated in environments 1500A-B. In some embodiments, one or more components of FIGS. 15A and 15B may be the same or similar to one or more other components described herein. In environment 1500A, user interface mechanism 1530 may include a knob 1554 that is rotatable in a first direction 1531-1 and a second direction 1531-2 to control flow in one or more embodiments described herein. In environment 1500B, user interface mechanism 1530 may include cam 1556 with cam profile 1558. In one or more embodiments, the cam 1556 may translate rotational motion of the knob 1554 into linear motion of the linkage 1560. In one or more such embodiments, vertical motion of the linkage 1560 may adjust one or more valve states. Embodiments are not limited in this context.

As opposed, or in addition, to using input comprising side-to-side motion to toggle between states/arrangements/functions, user interface mechanism 1530 may use rotational motion. In several embodiments, user interface mechanism 1530 may provide an ergonomic and comfortable rest of an operator's finger when in various positions. In some embodiments, user interface mechanism 1530 may include one or more portions of an atmospheric valve. For example, knob 1554 may include a through hole that can block flow through the atmospheric valve when covered, such as by a finger of an operator.

In some embodiments, the knob 1554 may be biased into the first position. For example, one or more torsional springs may maintain the knob 1554 in the first position. In many embodiments, rotating the knob 1554 in the first direction 1531-1 may cause a transition in a corresponding valve assembly from the first position to the second position. In many embodiments, rotating the knob 1554 in the second direction 1531-2 may cause a transition in a corresponding valve assembly from the first position to the third position. In one or more embodiments, transitions between different positions may be caused by the facets and/or geometry of the cam profile 1558 when rotated against linkage 1560.

Figure 16A:
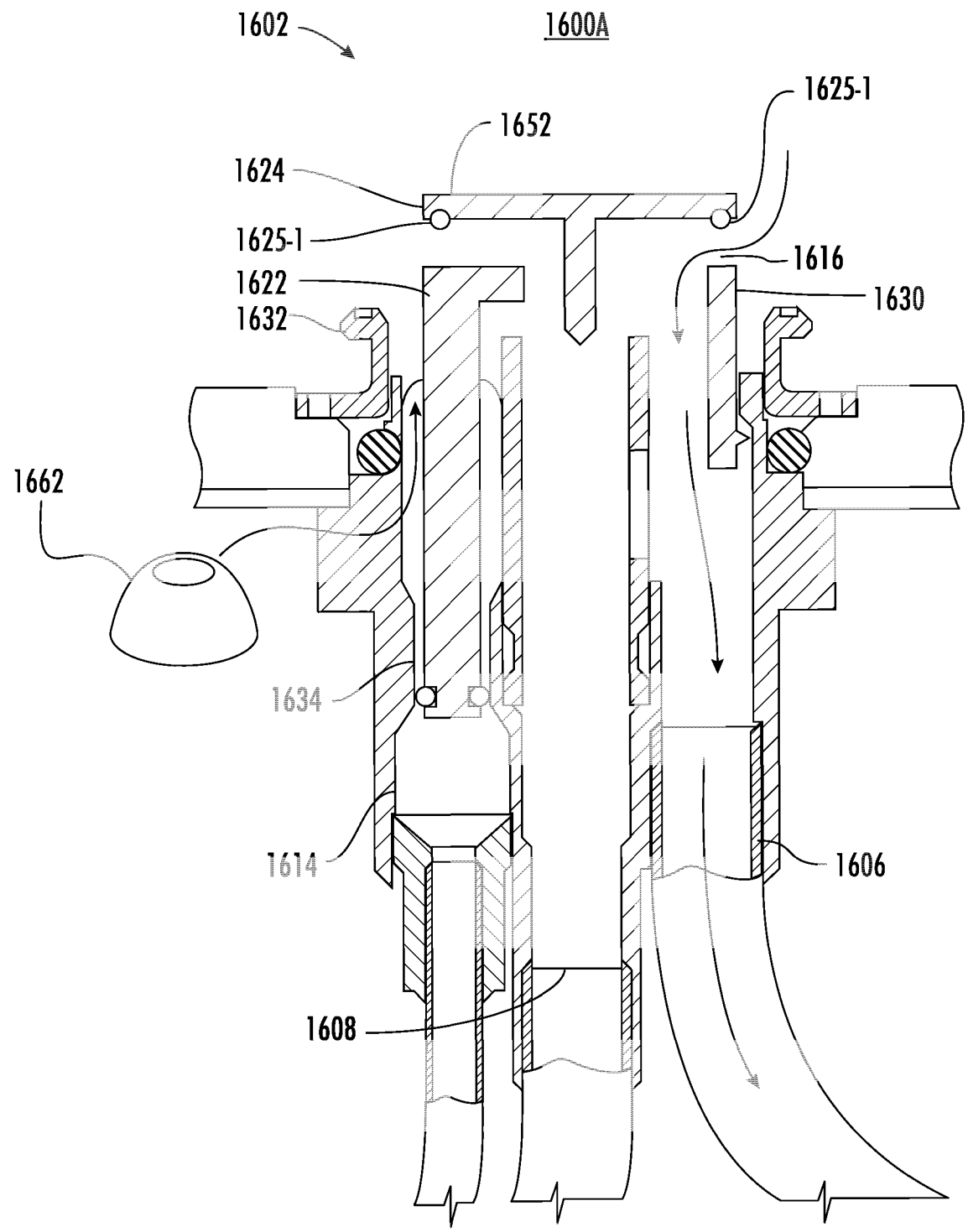
FIGS. 16A-16C illustrate various aspects of an exemplary suction valve assembly, according to one or more embodiments described herein.
Figure 16B:
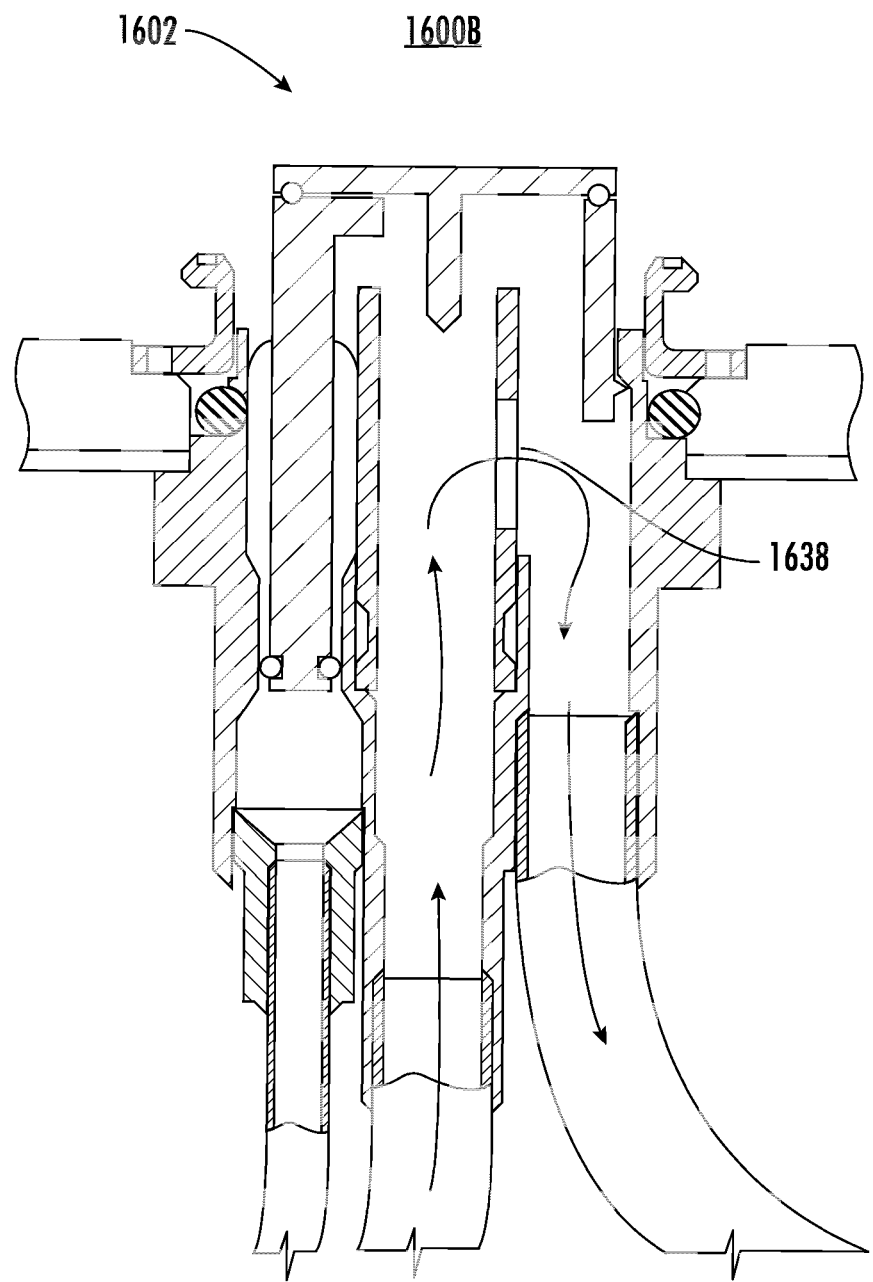
Figure 16C:
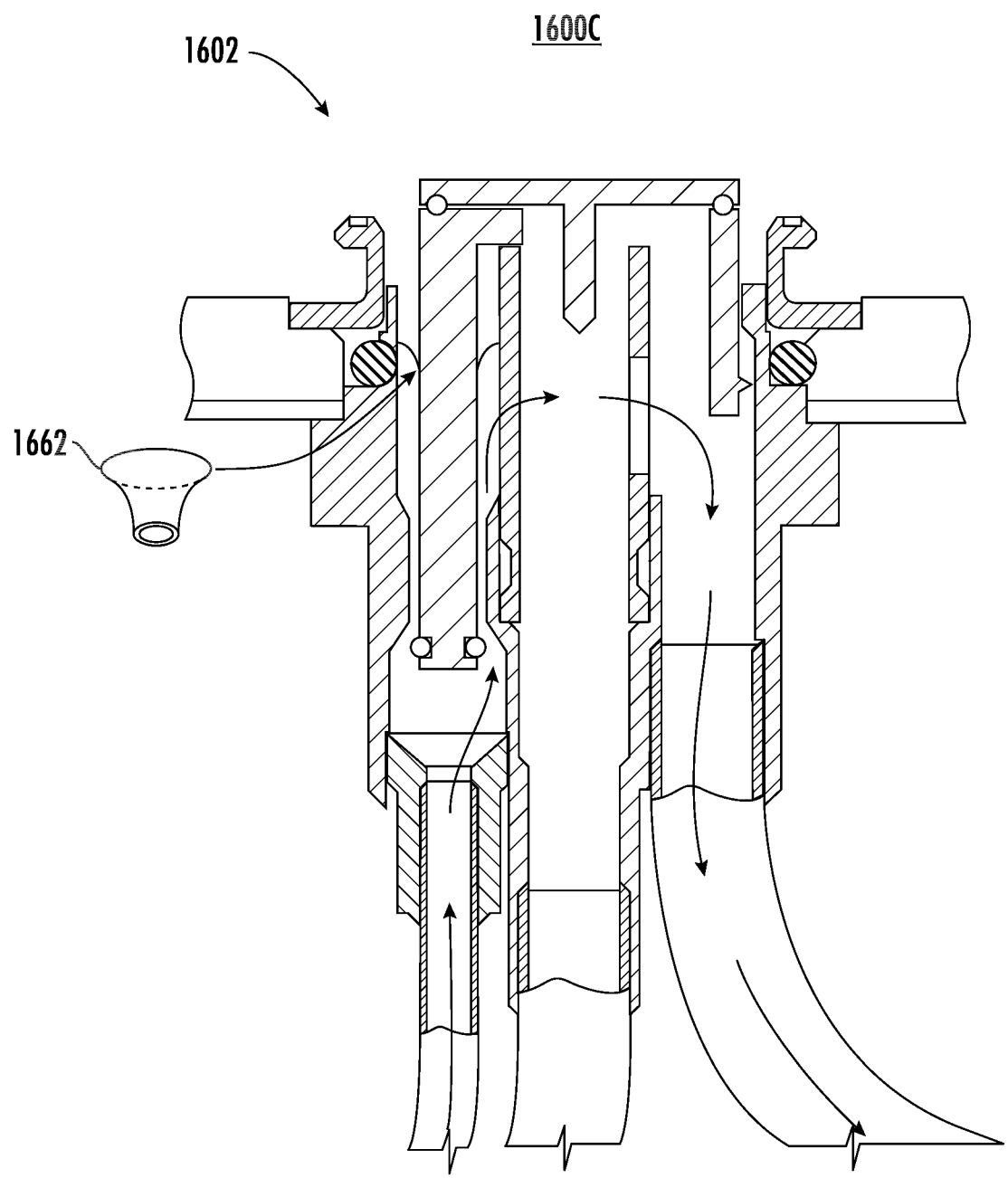

FIGS. 16A-16C illustrate various aspects of an exemplary suction valve assembly 1602 in environments 1600A-C, according to one or more embodiments described herein. In many embodiments, a cross section of one or more portions and/or components may be illustrated in environments 1600A-C. In some embodiments, one or more components of FIGS. 16A-16C may be the same or similar to one or more other components described herein. For example, one or more components of suction valve assembly 1302 may be the same or similar to one or more components of suction valve assembly 1602. Suction valve assembly 1602 includes balloon valve 1622, lip 1632, diaphragm switch 1662, necking portion 1634, balloon channel 1614, working channel 1608, atmospheric valves 1624-1, 1624-2, atmospheric channel 1616, and suction channel 1606. Environment 1600A may illustrate the suction valve assembly 1602 in a first position, environment 1600B may illustrate the suction valve assembly 1602 in a second position, and environment 1600C may illustrate the suction valve assembly 1602 in a third position. Embodiments are not limited in this context.

The illustrated embodiments of the suction valve assembly 1602 may utilize a diaphragm switch 1662 (e.g., a popper mechanism) to provide mechanical resistance within the valve. Accordingly, diaphragm switch 1662 may include one or more portions of biasing members, valves, and valve interface mechanisms. The energy to invert the diaphragm switch may require displacing the diaphragm toward the bottom of the valve well (see FIG. 16C). In several embodiments, the process of displacing downward may cause one or more valves to be opened or closed. For example, the process of displacing downward may cause a valve to be opened (e.g., balloon valve 1622) or close off suction from the atmosphere, such as part of a transition between positions or states. In some embodiments, the diaphragm switch 1662 may provide resistance until being inverted. In many embodiments, when the force associated with operator input is released, the diaphragm switch 1662 may pop back to the first position, displacing back upward, closing the valve that was opened (e.g., balloon valve 1622) or opening the seal being created for the vacuum.

In several embodiments, the diaphragm switch 1662, or popper mechanism, may lack bi-stability of the diaphragm switch (e.g., invert, but not stay inverted). In many such embodiments, the diaphragm switch 1662 may prevent the balloon valve from remaining open in the absence of a user input. In some embodiments, the diaphragm switch may provide tactile feedback (e.g., continuous resistance) through its entire range of motion. In these and other ways, suction valve assembly 1602 may provide intuitive and safe control (e.g., via user interface mechanism feedback). In many embodiments, one or more diaphragm switches may be utilized in suction valve assembly 1602 to provide a biasing member, such as to cause a valve or mechanism to return to an original state when not receiving input.

Figure 17A:
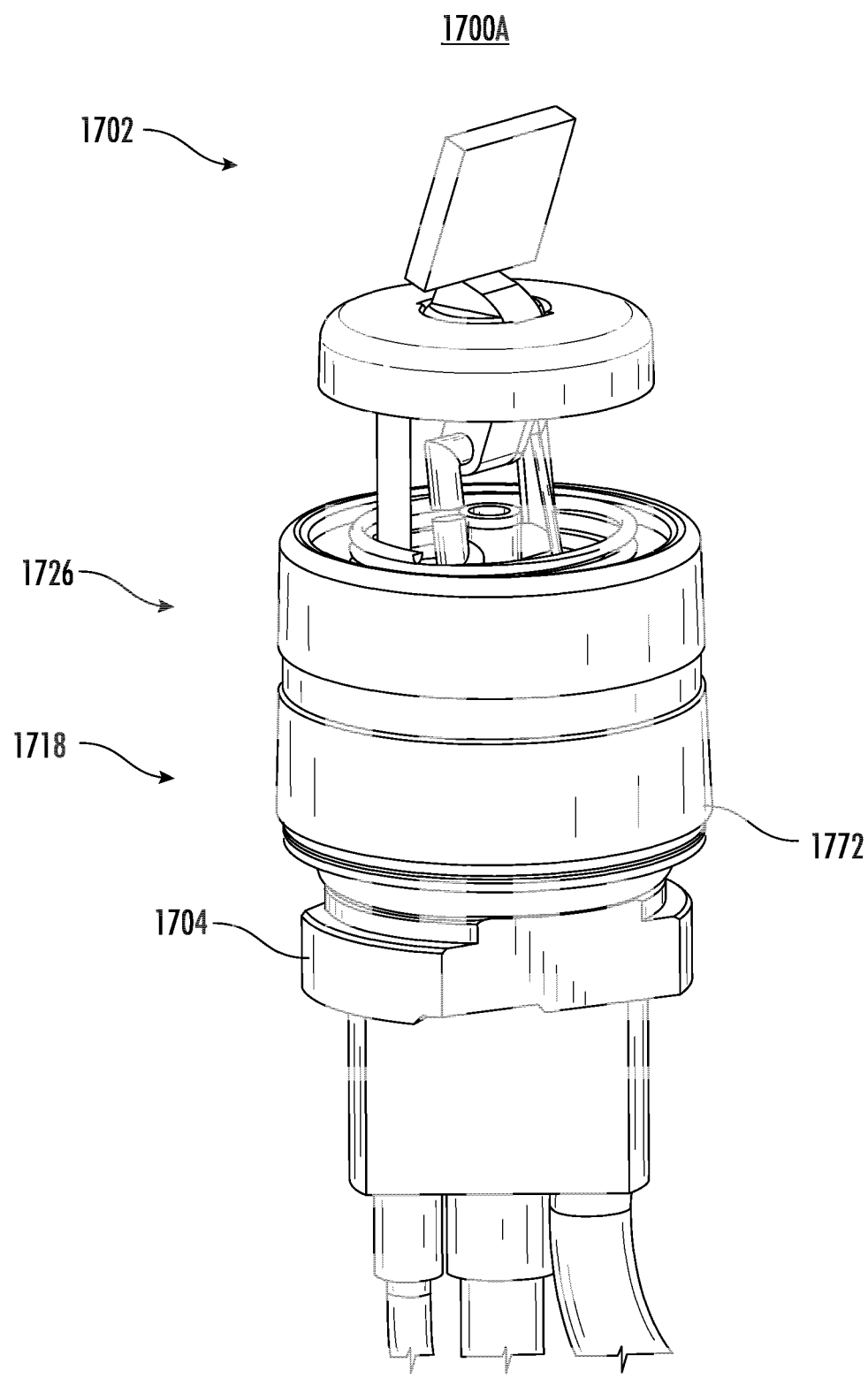
FIGS. 17A-17C illustrate various aspects of an exemplary suction valve assembly, according to one or more embodiments described herein.
Figure 17B:
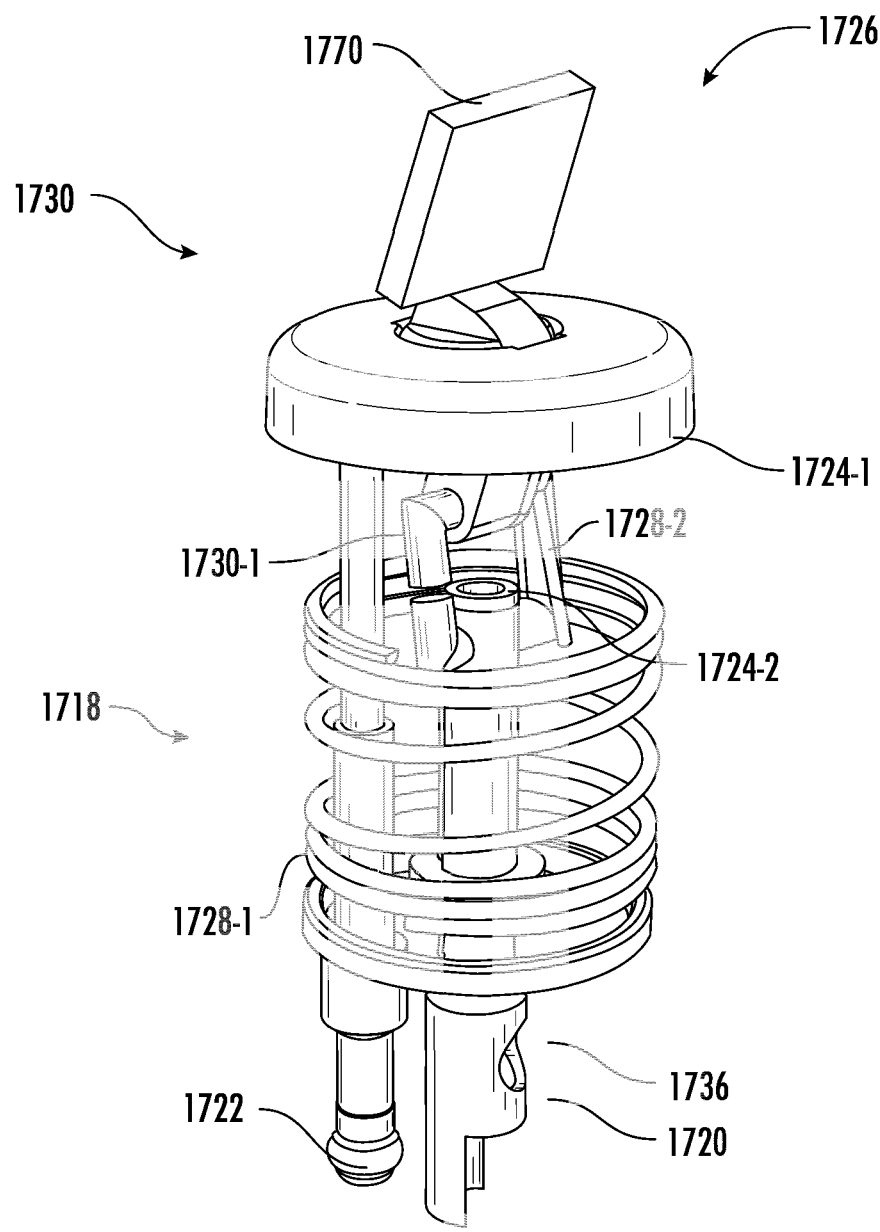
Figure 17C:
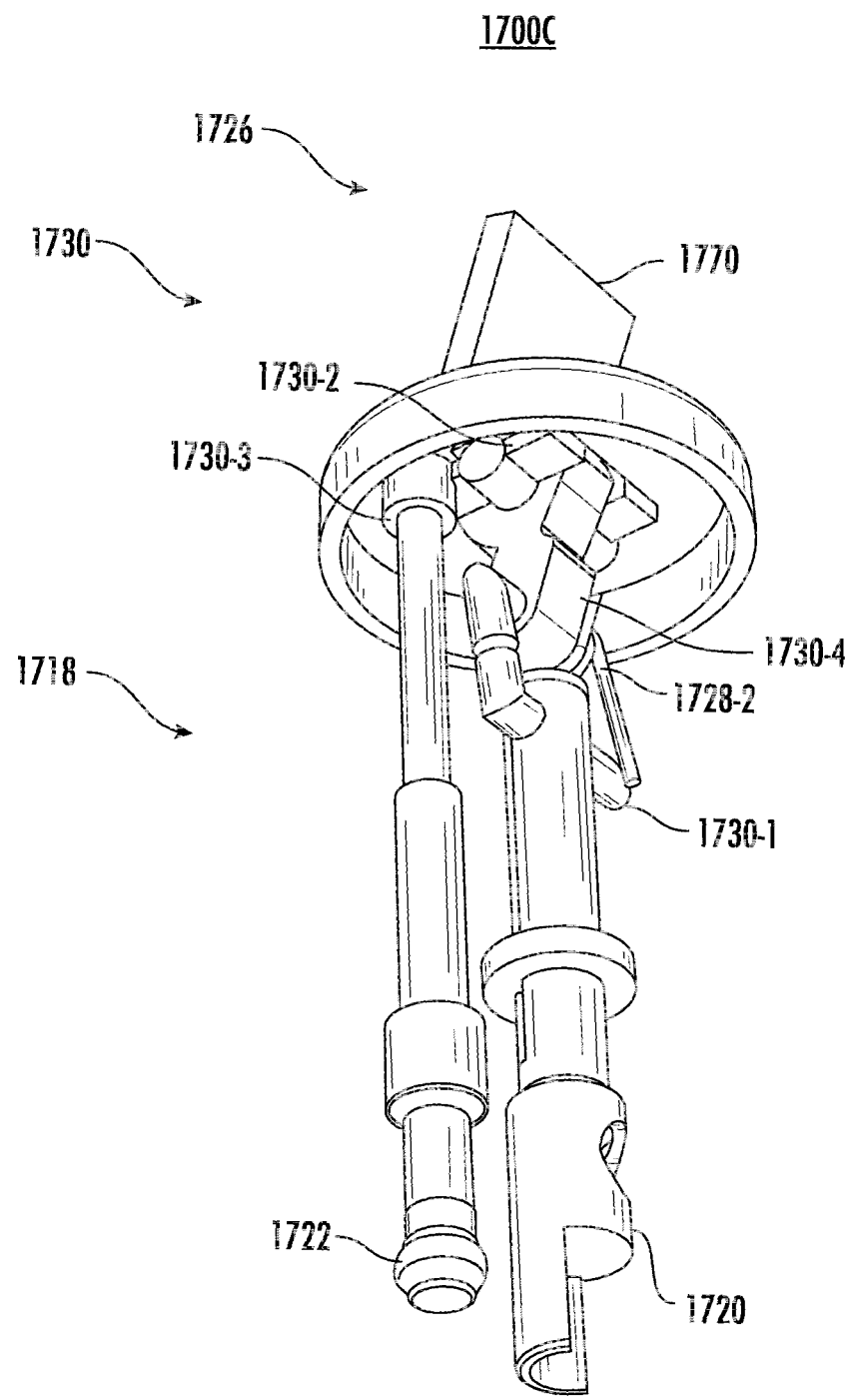

FIGS. 17A-17C illustrate various aspects of an exemplary suction valve assembly 1702 in environments 1700A-C, according to one or more embodiments described herein. In some embodiments, one or more components of FIGS. 17A-17C may be the same or similar to one or more other components described herein. In environment 1700A, suction valve assembly 1702 includes valve interface mechanism 1726, suction valve set 1718, and suction valve well 1704. Environment 1700B includes components of the suction valve assembly 1702 with the suction valve well 1704 and housing 1772 removed. The valve interface mechanism 1726 and suction valve set 1718 illustrated in environment 1700B include user interface mechanism 1730, linkage 1730-1, biasing members 1728-1, 1728-2, balloon valve 1722, working channel valve 1720 with well radial hole 1736, atmospheric valves 1724-1, 1724-2, and push-pull switch 1770. Environment 1700C includes a different view of the valve interface mechanism 1726 with biasing member 1728-1 removed. Embodiments are not limited in this context.

Referring to FIGS. 17B and 17B, environments 1700B, 1700C include valve interface mechanism 1726 including user interface mechanism 1730 and suction valve set 1718.

In the illustrated embodiments, user interface mechanism 1730 may be one or more of push-pull switch 1770, linkages 1730-1, 1730-2, 1730-3, 1730-4. At least a portion of one or more valves, such as atmospheric valve 1724-1 and biasing member set 1728 may include biasing members 1728-1, 1728-2. In some embodiments, the valve interface mechanism 1726 may include housing 1772.

In many embodiments, valve interface mechanism 1726 may be utilized to control flow through suction valve well 1704. In several embodiments, biasing member 1728-1 and/or 1728-2 may be utilized to bias one or more components into the first position. Accordingly, input received via the user interface mechanism 1730 (e.g., push-pull switch 1770 and/or atmospheric valve 1724-1) may position one or more of working channel valve 1720, balloon valve 1722, and atmospheric valves 1724-1, 1724-2. In various embodiments, the linkages 1730-1, 1730-2, 1730-3, 1730-4 may translate the push and pull motions of switch 1770 into controlled linear displacements to arrange one or more of working channel valve 1720, balloon valve 1722, and atmospheric valves 1724-1, 1724-2. In some embodiments, biasing member 1728-2 may position working channel valve 1720 in the first position in the absence of input being received. In several embodiments, one or more of up/down, forward/backward, and side-to-side motion may be provided as input to control flow via suction valve set 1718 and valve interface mechanism 1729.

In some embodiments, the user interface mechanism 1730 may operate as follows: in the first position (e.g., atmospheric suction state), the well radial hole 1736 aligns with the well radial hole 336 to allow flow from the suction channel to pull through atmospheric valve 1724-2 (see e.g., FIGS. 3B and 8A). Additionally, the balloon valve 1722 may seal the balloon channel in the first state (see e.g., FIG. 6B). In various embodiments, the suction valve assembly may be in the first position in the absence of user input.

To move to the second position (e.g., working channel suction state), a user depresses the push-pull switch (rotation) 1770 so that the bottom surface of 1770 is flush with the top surface of 1724-1. This causes the push-pull switch 1770 to rotate and move linkage 1730-1 upward against the force of biasing member 1728-2. When the push-pull switch 1770 is fully depressed, the atmospheric valve 1724-2 is held against the bottom surface of push-pull switch 1770 effectively sealing suction flow from atmosphere. This same motion draws the working channel valve 1720 upward, aligning the distal portion (i.e., portion with half a tube) with well radial hole 336. This allows suction flow from the working channel (see e.g., FIG. 3C).

To move to the third position (e.g., balloon channel suction state), the user linearly depresses atmospheric valve 1724-1 against biasing member 1728-1 (spring). This action forces working channel valve 1720 downward such that well radial hole 1736 is aligned with well radial hole 336 (FIG. 8A). Air does not flow from atmosphere in this state as it did in the first position because atmospheric valve 1724-1 is sealed against the push-pull switch. In the third position the balloon valve 1722 is also linearly depressed past the necking feature in the valve well allowing suction to flow from the balloon channel (see e.g., FIG. 3D).

Accordingly, in the illustrated embodiment, a pull causes rotation and then a push causes linear motion downward. However, other embodiments may include other configurations/motions. For example, such other configurations/motion may include a rotational push and a rotational pull (similar to rocker switch 1430-1 of FIG. 14) or a push causing rotation and then a linear push. In another example, the sequence may be changed to a linear push and then either a pull causing rotation or a push causing rotation.

The medical devices of the present disclosure are not limited and may include a variety of medical devices for accessing body passageways, including, for example, duodenoscopes, catheters, ureteroscopes, bronchoscopes, colonoscopes, arthroscopes, cystoscopes, hysteroscopes, EUS endoscopes, and the like. In various embodiments, the valve assemblies, or components thereof, described herein may include one or more (e.g., as a single or set of units) of a mounting point, mechanical coupler, bearing, seal, O-ring, actuator, valve, diaphragm, gasket, housing, connector, structural member, manifold, ergonomic features (e.g., finger/thumb grooves, padding, grip, application of mechanical advantage, and the like), spring, bellow, cantilever biasing member, torsional biasing member, linear biasing member, flapper valve, skirt, fin, disc, channel, cavity, lumen, and the like. In many embodiments, one or more components described herein may be constructed utilizing a variety of devices, technologies and/or processes, such as three-dimensional (3D) printing, multi-axis computer numeric control (CNC) machines, additive manufacturing, subtractive manufacturing, injection molding, computer aided design (CAD) programs, path planning programs, machining, forging, casting, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
    a valve well comprising a suction channel, a working channel, a balloon channel, and an atmospheric channel;
    a suction valve set including a working channel valve, a balloon valve, and an atmospheric valve, the working channel valve configured to control flow through the working channel of the valve well, the balloon valve configured to control flow through the balloon channel of the valve well, and the atmospheric valve configured to control flow through the atmospheric channel of the valve well,
    a valve interface mechanism including a set of one or more biasing members and a user interface mechanism, the user interface mechanism operable between a first state, a second state, and a third state, the first state comprising the suction valve set configured to place a suction channel of the valve well in fluid communication with the atmospheric channel, the second state comprising the suction valve set configured to place the suction channel in fluid communication with the working channel, and the third state comprising the suction valve set configured to place the suction channel in fluid communication with the balloon channel, wherein in the first state the working channel valve blocks flow through the working channel, the balloon valve blocks flow through the balloon channel, and the atmospheric valve permits flow through the atmospheric channel, wherein in the second state the working channel valve permits flow through the working channel, the balloon valve blocks flow through the balloon channel, and the atmospheric valve blocks flow through the atmospheric channel,
    wherein in the third state the working channel valve blocks flow through the working channel, the balloon valve permits flow through the balloon channel, and the atmospheric valve blocks flow through the atmospheric channel, and
    wherein the user interface mechanism comprises a lever coupled with the atmospheric valve and one or more linkages, the lever is configured to receive input causing the lever to pivot and the atmospheric valve to adjust to operate the user interface mechanism between the first state, the second state, and the third state.

2. The medical device of claim 1, wherein a transition from the first state to the second state produces tactile feedback via the lever.

3. The medical device of claim 1, wherein a transition from the second state to the third state produces tactile feedback via the lever.

4. A method of configuring the medical device of claim 1, comprising:
    configuring the suction valve set to place the suction channel of the valve well in fluid communication with the atmospheric channel of the valve well based on operation of the user interface mechanism to the first state;
    configuring the suction valve set to place the suction channel of the valve well in fluid communication with the working channel of the valve well based on operation of the user interface mechanism to the second state; and
    configuring the suction valve set to place the suction channel of the valve well in fluid communication with the balloon channel of the valve well based on operation of the user interface mechanism to the third state.

5. The method of claim 4, comprising producing tactile feedback via the user interface mechanism in response to operation of the user interface mechanism to one or more of the first state, the second state, and the third state.

* * * * *